United States Patent [19]
Bowditch et al.

[11] Patent Number: 5,939,524
[45] Date of Patent: Aug. 17, 1999

[54] PLATELET GPIII Pl$^{A1}$ AND Pl$^{A2}$ EPITOPES, THEIR PREPARATION AND USE

[75] Inventors: Ronald D. Bowditch, Encinitas; Robert McMillan, Del Mar; Mark H. Ginsberg, San Diego, all of Calif.

[73] Assignee: The Scripps Research Institute, LaJolla, Calif.

[21] Appl. No.: 07/808,457

[22] Filed: Dec. 9, 1991

[51] Int. Cl.$^6$ .......................... A61K 38/00; A61K 35/14; C07K 5/00; C07K 1/00
[52] U.S. Cl. .......................... 530/324; 530/300; 530/350; 530/380; 530/381
[58] Field of Search .................................... 530/350, 409, 530/324, 300, 380, 381; 435/69.3

[56] References Cited

U.S. PATENT DOCUMENTS

| | | |
|---|---|---|
| 3,654,090 | 4/1972 | Wilhelmus et al. |
| 3,850,752 | 11/1974 | Schuurs et al. |
| 4,016,043 | 4/1977 | Schuurs et al. |
| 4,356,270 | 10/1982 | Itakura . |
| 4,374,120 | 2/1983 | Soini et al. |
| 4,403,036 | 9/1983 | Hartley et al. |
| 4,416,988 | 11/1983 | Rubin . |
| 4,493,795 | 1/1985 | Nestor, Jr. et al. |
| 4,569,790 | 2/1986 | Koths et al. |
| 4,599,230 | 7/1986 | Milich et al. |
| 4,599,231 | 7/1986 | Milich et al. |
| 4,631,211 | 12/1986 | Houghten . |
| 4,683,136 | 7/1987 | Milich et al. |
| 4,683,195 | 7/1987 | Mullis et al. |
| 4,683,202 | 7/1987 | Mullis . |
| 4,707,404 | 11/1987 | Morishita et al. |
| 4,714,681 | 12/1987 | Reading . |
| 4,818,678 | 4/1989 | Oldstone et al. |
| 4,828,527 | 5/1989 | Thornton et al. |
| 4,882,145 | 11/1989 | Thornton et al. |
| 5,091,302 | 2/1992 | Newman et al. |

FOREIGN PATENT DOCUMENTS 9006953  6/1990  WIPO .

OTHER PUBLICATIONS

Blanchette et al., *Curr. STud. Hematol. Blood Transf.*, 52:87 (1986).
Kunicki et al., *Mol. Immunol.*, 16:353 (1979).
Newman et al., *J. Clin. Inves.*, 83:1778 (1989).
Goldberger et al., *Blood*, 76:681 (1989).
Flug et al., *Blood*, 77:1964 (1991).
Newman et al., *Mol. Immunol.*, 22:719 (1985).
Calvette et al., *Biochem J.*, 250:697 (1988).
Beer et al., *J. Biol. Chem.*, 264:17564 (1989).
Calvette et al., *Biochem. J.*, 273:63 (1991).
Newman, *Thromb Haemostas*, 66:111 (1991).
Matteuci et al., *Jacs.* 103:3185 (1981).
Studier et al., *Proc. Natl. Acad. Sci. USA.* 86:69147–21 (1989).
Sommer et al., *Nuc. Acid. REs.*, 17:6749 (1989).
Narrang et al., *Meth. Enzymol.*, 68:90 (1979).
Itakura et al., *Ann. Rev. Biochem.*, 53:323–56 (1989).
Brown et al., *Meth. Enzymol.*, 68:109 (1979).
Bukhrashvili et al., *Biochem. Biophys. Acta*, 1008:102 (1989).
Elie et al., *Biochem. Biophys. Acta*, 951:261 (1988).
Mullis et al., *Methods in Enzymol.*, 155:335 (1987).
Southern, *J. Mol. Biol.*, 98:503 (1975).
Sorge et al., *Mol. Cell. Biol.*, 4:1730–37 (1984).
Better et al., *Science*, 240:1041–1043 (1988).
Skerra et al., *Science*, 240:1030–1041 (1988).
Orlandi et al., *Proc. Natl. Acad. Sci. USA*, 86:3833–3837 (1989).
Klipstein et al., *J. Infect. Dis.*, 147:318–326 (1983).
Galfre et al., *Meth. Enzymol.*, 73:3–46 (1981).
Avrameas et al., *Scand. J. Immunol.* 8(7): 7–23, (1978).
Rodwell et al., *Biotech.*, 3:889–894 (1984).
Woods et al., *Blood*, 63:368 (1984).
O'Toole et al., *Blood*, 74:14 (1989).
Young et al., *Proc. Nat. Acad. Sci. USA*, 80:1194 (1983).
Loftus et al., *Science*, 249:915 (1990).
Sanger et al., *Proc. Natl. Acad. Sci., USA*, 74:5463 (1977).
Zoller et al., *Nuc. Acids. Res.*, 10:6487 (1982).
Kunkel et al., *Proc. Natl. Acad. Sci., USA*, 82:488 (1985).
Amann et al., *Gene*, 25:167–178 (1983).
Brosius et al., *Proc. Natl. Acad. Sci. USA*, 81:6929–6933 (1984).
Farabaugh, *Nature*, 274:765–769 (1978).
Yanisch–Perron et al., *Gene*, 33:103 (1985).
Guan et al., *Gene*, 67:21–30 (1987).
Duplay et al., *Biol. Chem.*, 259:10606–10613 (1984).
Barron–Casella et al., *Blood*, 84(4):1157–1163 (Aug. 15, 1994).
A. White et al., *Principles of Biochemistry*, Sixth ed., McGraw–Hill Book Co., New York (1978) pp. 106–107.
Sheer et al., Cancer Research 48(23):6811–6818, Dec. 1988.
Sambrook, J. "Molecular Cloning, A Laboratory Manual" 2nd Edition published in 1989 by Cold Spring Harbor Laboratory Press (NY); see Chapter 12 and Chapter 17 (specifically 17.1–17.9).
Mierendorf, R.C. et al. (1987) Methods in Enzymology 152:458–469.
Bodary, S.C. et al. (1989) J. Biol. Chem. 264:18859–18862.
Fitzgerald, L.A. et al. (1987) J. Biol. Chem. 262:3936–3939.
Zimrin, A.B. et al. (1990) J. Biol. Chem. 265:8590–8595.
Zimrin, A.B. et al. (1988) J. Clin. Intrest. 81:1470–1475.
Rosa, J.P. et al. (1989) Blood 72:593–600.
Uhlen, M. et al. (1990) Methods in Enzymology 185:129–143.

*Primary Examiner*—Anthony C. Caputa
*Assistant Examiner*—Mark Navarro
*Attorney, Agent, or Firm*—Welsh & Katz, Ltd.

[57] ABSTRACT

Polypeptides and fusion polypeptides that immunologically mimic the native Pl$^{A1}$ and Pl$^{A2}$ determinants of platelet protein GPIIIa are disclosed. Also disclosed are DNA segments and recombinant DNA molecules that encode those polypeptides and fusion polypeptides and methods for expressing and using those determinants. Antibodies that immunoreact with one determinant or the other, but not both are also disclosed, as are methods of preparing and using those antibodies.

3 Claims, 1 Drawing Sheet

M R A R P R P R P L W V T V L A L G A L A G V

G V G G P N I C T T R G V S S C Q Q C L A V S
                                P
P M C A W C S D E A L P L G S P R C D L K E N

L L K D N C A P E S I E F P V S E A R V L E

PLATELET GPIII PI^{A1} AND PI^{A2} EPITOPES, THEIR PREPARATION AND USE

This invention was made with government support under Contract Nos. AR 27214, HL 37945 and HL 16411 awarded by the National Institutes of Health. The government has certain rights in the invention.

DESCRIPTION

TECHNICAL FIELD

The present invention relates to the platelet surface glycoprotein referred to as GPIIIa, and more particularly to tertiary structure-dependent antigen denominated PI^A that is part of the GPIIIa molecule, their preparation and use.

BACKGROUND ART

The platelet antigen system, PI^A, is associated with two clinical syndromes, neonatal alloimmune thrombocytopenia (NAIT) and posttranfusion purpura (PTP) [Aster, *The immunologic thrombocytopenias*, Kunicki and George, eds., *Platelet Immunobiology*, 387, Philadelphia, Pa. (1989)]. NAIT is a bleeding disorder of newborns with increased platelet destruction caused by tranplacentally transfered maternal platelet specific antibodies and is estimated to occur at a frequency of 1/1,000 births [Blanchette et al., *Curr. Stud. Hematol. Blood Tranf.*, 52:87 (1986)]. PTP is an antibody-mediated thrombocytopenia in response to platelet incompatibility following a blood tranfusion. The most common cause of both NAIT and PTP in the Caucasian population is the PI^{A1} alloantigen.

The alloantigenic determinant responsible for eliciting anti-PI^{A1} antibodies is present on the platelet membrane GPIIIa [Kunicki et al, *Mol. Immunol.*, 16:353 (1979)]. The PI^{A1} and PI^{A2} phenotypes are dependent on the presence of a thymidine (T) or cytidine (C), respectively, at base 196 of the GPIIIa cDNA sequence [Newman et al, *J. Clin. Inves.*, 83:1778 (1989)].

The T→C base change results in a leucine/proline polymorphism at residue 33 of mature GPIIIa. Although the leucine to proline polymorphism at the amino terminal end of GPIIIa is responsible for the PI^{A1}/PI^{A2} platelet allotypes [Goldberg et al., *Blood*, 78:681 (1989)], synthetic linear peptides containing this polymorphism [Flug et al, *Blood*, 77:1964 (1991)] did not react with anti-PI^{A1} antibodies, suggesting that the leucine$^{33}$/proline$^{33}$ polymorphism might affect global folding or post-translational processing to assemble the PI^{A1} epitope.

SUMMARY

In one aspect, the present invention relates to an isolated DNA molecule containing about 195 to 800 nucleotide base pairs that encodes an amino acid residue sequence of GPIIIa that includes the PI^{A1} determinant. Preferably, that DNA molecule has the nucleotide base sequence of SEQ ID NO:2, SEQ ID NO:6, SEQ ID NO:10, SEQ ID NO:12, SEQ ID NO:14, SEQ ID NO:16, or SEQ ID NO:18.

The present invention also relates to an isolated DNA molecule containing about 195 to 800 nucleotide base pairs that encodes an amino acid residue sequence of GPIIIa that includes the PI^{A2} determinant, which DNA molecule has the nucleotide base sequence of SEQ ID NO:4, SEQ ID NO:8, SEQ ID NO:20, SEQ ID NO:22, SEQ ID NO:24, SEQ ID NO:26 or SEQ ID NO:28.

In another aspect, the present invention relates to a recombinant molecule comprising an expression vector operatively ligated to an exogenous DNA segment that encodes an amino acid residue sequence of the PI^{A1} or PI^{A2} determinant of platelet GPIIIa, which recombinant molecule when transformed into a host cell expresses either the native platelet GPIIIa PI^{A1} or PI^{A2} determinant. The exogenous DNA segment used in the recombinant molecule is preferably an isolated DNA molecule as set forth above. A preferred expression vector is λgt22.

In another aspect, the present invention relates to a method for preparing a polypeptide that contains the native platelet GPIIIa PI^{A1} or PI^{A2} determinant that comprises culturing host cells transformed with a recombinant molecule that comprises an expression vector operatively ligated to an exogenous DNA segment that encodes an amino acid residue sequence shown in SEQ ID NO:1 from about residue 1 through about residue 65; and maintaining the transformed host cells under culture conditions for a time period sufficient for the polypeptide to be expressed. Preferred host cells are *E. coli*. A preferred vector is λgt22 and a preferred exogenous DNA segment is selected from the group having SEQ ID NO's:2, 4, 6, 8, 10, 12, 14, 16, 18, 20, 22, 24, 26 and 28. The polypeptide can be expressed as a fusion polypeptide.

Still further, the present invention relates to an isolated polypeptide that contains about 65 to 266 amino acid residues of the platelet GPIIIa including the amino acid residue sequence of SEQ ID NO:1 and which polypeptide exhibits the platelet GPIIIa PI^{A1} or PI^{A2} determinant. Preferably, the isolated polypeptide has an amino acid residue sequence selected from the group consisting of SEQ ID NO's:3, 5, 7, 9, 11, 15, 17, 19, 21, 23, 25, 27 and 29.

The present invention also relates to a fusion polypeptide that immunologically mimics the native platelet GPIIIa PI^{A1} or PI^{A2} determinant that comprises a first polypeptide operatively linked to a second polypeptide. The first polypeptide defines the amino acid residue sequence of an immunologically inert polypeptide or protein peptide-bonded to the second polypeptide. The second polypeptide contains about 65 to 266 amino acid residues of platelet GPIIIa, including the amino acid residue sequence of SEQ ID NO:1 and exhibits the native platelet GPIIIa PI^{A1} or PI^{A2} determinant. In preferred embodiment, the first polypeptide has the amino acid sequence of β-galactosidase and the second polypeptide has an amino acid residue sequence selected from the group consisting of SEQ ID NO's:3, 5, 7, 9, 11, 13, 15, 17, 19, 21, 23, 25, 27 and 29.

In yet another aspect, the present invention relates to a method of assaying a human antibody-containing body sample for the presence of human antibodies that immunoreact with the native GPIIIa PI^{A1} or PI^{A2} determinant, which method comprises:

(a) forming an aqueous immunoreaction admixture by admixing the body sample with an antigen that is
    (i) an isolated polypeptide having the sequence of GPIIIa and containing about 65 to 266 amino acid residues that exhibits the native PI^{A1} or PI^{A2} determinant and includes the amino acid residue sequence of SEQ ID NO:1, or
    (ii) a fusion polypeptide that includes an amino acid residue sequence of about 65 to 266 amino acid residues of GPIIIa exhibits the native PI^{A1} or PI^{A2} determinant and that includes the amino acid residue sequences of SEQ ID NO:1;
  (b) maintaining the aqueous immunoreaction admixture under biological assay conditions for a time period sufficient for any of the antibodies present to immunoreact with the antigen to form an immunoreaction product; and (c) detecting the presence of any of the immunoreaction product formed and thereby the presence of the antibodies.

Where the determinant is the native GPIIIa Pl$^{A1}$ determinant, the antigen is selected from the group consisting of SEQ ID NO:3, SEQ ID NO:7, SEQ ID NO:11, SEQ ID NO:13, SEQ ID NO:15, SEQ ID NO:17, SEQ ID NO:19 and SEQ ID NO:11 operatively linked to the carboxy-terminal end of β-galactosidase.

Where the determinant is the native GPIIIa Pl$^{A1}$ determinant, the antigen is selected from the group consisting of SEQ ID NO:5, SEQ ID NO:9, SEQ ID NO:21, SEQ ID NO:23, SEQ ID NO:25, SEQ ID NO:27, SEQ ID NO:29 and SEQ ID NO:21 operatively linked to the carboxy-terminal end of β-galactosidase.

In a preferred embodiment, detecting is accomplished by:

(i) admixing the immunoreaction product with second antibodies immunoreactive with human antibodies to form a second admixture, which second antibodies are operatively linked to a marker;

(ii) maintaining the second admixture under biological assay conditions for a period of time sufficient for the second antibodies to immunoreact with the human antibodies to form a second immunoreaction product; and (iii) determining the amount of marker affixed to the second immunoreaction product, thereby determining the presence of human antibodies that immunoreact with the native GPIIIa Pl$^{A1}$ or Pl$^{A2}$ determinant. Preferably, the marker is selected from the group consisting of radioactive, enzyme, biotin, fluorescent, and chemiluminescent labels and the antigen is affixed to a solid support prior to the admixture of human body fluid sample and antigen.

In a still further aspect, the present invention relates to a method for typing platelets that comprises (a) admixing platelets from a donor in an aqueous medium with antibodies that immunoreact with one or the other but not both of the GPIIIa Pl$^{A1}$ and Pl$^{A2}$ determinants to form an aqueous immunoreaction admixture;

(b) maintaining the aqueous immunoreaction admixture under biological reaction conditions for a time period sufficient for the antibodies to immunoreact and form an immunoreaction product; and (c) detecting the presence of any of the immunoreaction product and thereby the presence of one or the other of said GPIIIa Pl$^{A1}$ or Pl$^{A2}$ determinants and the platelet type.

In alternate preferred embodiments, the antibodies (a) immunoreact with the GPIIIa Pl$^{A1}$ determinant and not the GPIIIa Pl$^{A2}$ determinant, or (b) immunoreact with the GPIIIa Pl$^{A2}$ determinant and not the GPIIIa Pl$^{A1}$ determinant. Preferably, the antibodies are monoclonal antibodies.

In another aspect, the present invention relates to a diagnostic assay system in kit form for typing platelet GPIIIa Pl$^{A}$ determinants comprising a package containing antibodies that immunoreact with one of the platelet GPIIIa Pl$^{A1}$ or Pl$^{A2}$ determinants but not both determinants in a amount sufficient for at least one assay, and a label for detecting the immunoreaction of said antibodies with platelets. The diagnostic system can further include a second package containing antibodies that immunoreact with the other of the platelet GPIIIa Pl$^{A1}$ or Pl$^{A2}$ determinants but not both determinants in an amount sufficient for at least one assay. Preferably, the label is linked to the antibodies.

Still further, the present invention relates to a diagnostic assay system in kit form for assaying for the presence of human antibodies to platelet GPIIIa Pl$^{A1}$ or Pl$^{A2}$ determinants comprising:

(a) a package containing an antigen that is
 (i) an isolated polypeptide having the sequence of GPIIIa and containing about 65 to 266 amino acid residues that exhibits the native Pl$^{A1}$ or Pl$^{A2}$ determinant and includes the amino acid residue sequence of SEQ ID NO:1, or
 (ii) a fusion polypeptide that includes an amino acid residue sequence of about 65 to 266 amino acid residues of GPIIIa exhibits the native Pl$^{A1}$ or Pl$^{A2}$ determinant and that includes the amino acid residue sequences of SEQ ID NO:1;

the antigen being present in an amount sufficient for carrying out at least one assay; and (b) a means for detecting the immunoreaction of the human antibodies with the antigen.

Preferably, the antigen has an amino acid residue sequence selected from the group consisting of SEQ ID NO's:3, 5, 7, 9, 11, 13, 15, 17, 19, 21, 23, 25, 27, 29 and 11 or 21 operatively linked to the carboxy-terminal end of a β-galactosidase and the antigen is affixed to a solid support. The means for detecting the immunoreaction of the human antibodies are anti-human antibodies from another species linked to a label.

BRIEF DESCRIPTION OF THE DRAWINGS

In the drawings forming a portion of this disclosure.

Definitions

Figures 1, 2:
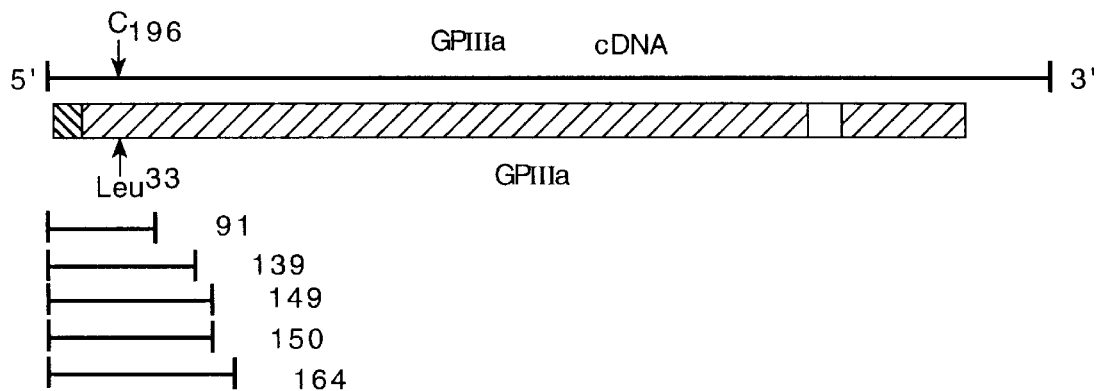
FIG. 1 illustrates a schematic representation of the full length platelet GPIIIa cDNA used for construction of the λgt22 expression library (black bar at the top) and of the protein encoded (grey box). The signal sequence (black box) and transmembrane domain (white box) of the encoded protein are also depicted within the gray box. Regions of GPIIIa cDNA isolated from the λgt22 expression library with anti-Pl$^{A1}$ antibodies are depicted as bars below the schematically depicted encoded protein, with the number of residues encoded by each cDNA shown to the right of each bar.
FIG. 2 illustrates the amino acid residue sequence in single letter code encoded by the smallest expressed isolated clone that reacted with anti-Pl$^{A1}$ antibodies (SEQ ID NO's:11 and 13). The signal sequence of the protein is underlined, cysteines (C) are boxed, the leucine$^{33}$/proline$^{33}$ polymorphism is indicated by the arrow between L and P, and the sequence of the 13-residue linear peptide described by Flug et al., *Blood*, 77:1964 (1991) that did not react with anti-Pl$^{A1}$ antibodies is noted by a dotted line under the sequence.

Amino Acid Residue Sequence: a series of two or more amino acid residues joined via peptide linkages between adjacent residues to form a peptide or polypeptide. An amino acid residue sequence is conveniently represented by the one or three letter abbreviations for its constituent amino acids. The abbreviations used herein for amino acids are those provided at 37 C.F.R. §1.822(b)(2) and are reproduced in the following table of correspondence:

| ABBREVIATION | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | GlU | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unspecified |

The individual residues comprising an amino acid residue sequence herein are in the L isomeric form. Also, the amino acid residue sequence can include post-translationally modified amino acids, e.g., hydroxylated, glycosylated amino acid residues, or residues linked via disulfide bonds. In addition, an amino acid residue sequence can include one or more modified or unusual amino acids, such as those listed in 37 C.F.R. §1.822(b)(4), which are incorporated herein by reference. An amino acid residue sequence can be represented by the abbreviations corresponding to its constituent amino acids.

Antibody: A polypeptide or protein that immunologically binds to a ligand. Antibodies, as used herein, are immunoglobulin molecules and immunologically active fragments of immunoglobulin molecules. Such portions known in the art as Fab, Fab'; F(ab')$_2$ and F$_V$ are included. Typically, antibodies bind ligands that range in size from about 6 through about 34 Å with association constants in the range of about $10^4$ to $10^{10}$ M$^{-1}$, and as high as $10^{13}$M$^{-1}$. Antibodies can bind a wide range of ligands, including small molecules such as steroids and prostaglandins, biopolymers such as nucleic acids, proteins and polysaccharides, and synthetic polymers such as polypropylene. An "antibody combining site" is that structural portion of an antibody molecule comprised of a heavy and light chain variable and hypervariable regions that specifically binds (immunoreacts with) antigen. The term "immunoreact" in its various forms is used herein to refer to binding between an antigenic determinant-containing molecule (antigen) and a molecule containing an antibody combining site such as a whole antibody molecule or a portion thereof. An "antigenic determinant" is the structural portion of the antigen that is immunologically bound by an antibody combining site. The term is also used interchangeably with "epitope" and "determinant". Antibodies can bind a single epitope of an antigen (monoclonal) or multiple epitopes (polyclonal). Antibodies that are induced by a polypeptide often immunoreact with a plurality of epitopes that are fewer in number than the number of epitopes that react with polyclonal antibodies as are formed from a protein immunogen. Such polypeptide-induced antibodies are referred to herein as oligoclonal antibodies.

Fusion protein or Polypentide: A protein or polypeptide containing amino acid residue sequences from each of two distinct proteins; it is formed by the expression of a recombinant gene in which two coding sequences have been joined together such that their reading frames are in frame. A fusion protein results when the expressed material contains at least one complete protein sequence, whereas only portions of the proteins are present in a fusion polypeptide. Hybrid genes of this type can be constructed in vitro, e.g. in order to label the product of a particular gene with a protein which can be more readily assayed. For example, if a gene is fused to lacZ in Escherichia coli, a fusion protein or polypeptide with β-galactosidase activity or a partial sequence can be obtained. Alternatively, a protein can be linked to an exogenous signal peptide to allow its secretion by the cell. The above distinction between a fusion protein and fusion polypeptide notwithstanding, the term fusion polypeptide will be usually used herein for both types of molecule except where a specific fusion protein is discussed.

Ligand: A molecule having a structural region that binds specifically to a particular receptor molecule, usually via electrostatic forces and/or hydrogen bonds. An exemplary receptor molecule is an antibody combining site.

Oligonucleotide/Polynucleotide/DNA Segment: A polymer of single or double stranded nucleotides. As used herein, these terms and their grammatical equivalents, can be composed of a naturally-occurring nucleic acid, e.g., adenosine (A), cytidine (C), guanosine (G), thymidine (T), uridine (U), inosine (I), as well as a modified base, as presented at 37 C.F.R. §1.82 (p)(1).

Peptide/Polypeptide: A polymer comprising at least two amino acid residues in which adjacent residues are connected by a peptide bond between the alpha-amino group of one residue and the alpha-carbonyl group of an adjacent residue. The primary structure of a polypeptide has a primary amine group at one terminus and a carboxylic acid group at the other terminus of the polymer. Thus, a polypeptide may be represented by the formula:

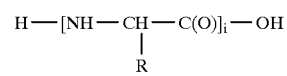

where R is a side chain characteristic of a given amino acid residue and i indicates the number of amino acid residues comprising the polymer which number is two or more. A polypeptide can comprise one or more different amino acid residue sequences as in the case of a fusion polypeptide. Also, a polypeptide in aqueous solution is usually in one or more zwitterionic forms depending on the pH of the solution.

Protein: A single polypeptide or set of cross-linked polypeptides comprising more than about 50 amino acid residues. Proteins can have chemical crosslinking, e.g., via disulfide bridges, within the same polypeptide chain or between adjacent polypeptides. When a protein is glycosylated it may be called a glycoprotein, as is the case of GPIIIa discussed herein.

Receptor: A biologically active proteinaceous molecule having a structural region that specifically binds to (or with) another molecule (ligand). An antibody combining site is one type of receptor.

Vector: A DNA molecule capable of autonomous replication in a cell and to which a DNA segment, e.g., gene or polynucleotide, can be operatively ligated so as to bring about replication of the attached segment. An expression vector is capable of directing expression of a DNA segment encoding one or more polypeptides in a suitably transformed host cell when the DNA segment is under the control of a promoter sequence of the vector.

DETAILED DESCRIPTION OF THE INVENTION

A. Introduction

The results of the work related to this invention have two major implications. First, the alloantigenic epitope for anti-$Pl^{A1}$ and -$Pl^{A2}$ antibodies is shown herein to be located in the amino-terminal 65 residues of mature GPIIIa. Previous studies have presented evidence that the leucine$^{33}$/proline$^{33}$ amino acid polymorphism is responsible for the two $Pl^A$ phenotypes [Newman et al., *J. Clin. Invest.*, 83:1778 (1989); Goldberger et al., *Blood*, 78:681 (1991)], however, identification of the polymorphism does not define the epitope for the alloantibodies of clinical interest.

There have been conflicting reports as to the location of the $Pl^{A1}$ epitope by utilizing proteolytic methods [Newman et al., *Mol. Immunol.*, 22:719 (1985); Calvette et al., *Biochem J.*, 250:697 (1988); Beer et al., *J. Biol. Chem.*, 264:17564 (1989); Flug et al., *Blood*, 77:1964 (1991)]. Although the evidence suggested that the $Pl^{A1}$ epitope was located in proximity to the polymorphism, recent studies utilizing synthetic peptides that spanned the polymorphism (FIG. 2) showed that the synthetic peptide failed to bind anti-$Pl^{A1}$ antibodies and anti-peptide antibodies failed to distinguish the two phenotypes [Flug et al., *Blood*, 77:1964 (1991)]. The data presented here indicate that the epitope for anti-$Pl^{A1}$ and -$Pl^{A2}$ antibodies resides in the amino terminal 7 kDa of GPIIIa and within 33 residues of the actual polymorphism responsible for the $Pl^A$ phenotype. The data herein along with that of Flug et al. indicate that the $Pl^{A1}$ and $Pl^{A2}$ epitopes are non-linear, and depend upon the folding of the GPIIIa molecue and its $Pl^A$-containing determinant; i.e., those epitopes are tertiary structure-dependent.

The second major finding in this study is that the $Pl^{A1}$ and $Pl^{A2}$ epitopes can be expressed in a prokaryotic system. Utilization of a prokaryotic expression system for characterizing the $Pl^A$ epitopes preserves the disulfide bonds necessary for expression of the reduction sensitive epitopes [Blanchette et al., *Curr. Stud. Hematol. Blood Tranf.*, 52:87 (1986)].

Seven cysteines exist in the small platelet GPIIIa fragment identified in this study (FIG. 2) indicating that local sulfhydryl bonding between these residues [Calvete et al., *Biochem. J.*, 273:63 (1991)] is involved in formation of the epitope and that the cysteine$^5$-cysteine$^{435}$ disulfide bond is not required. These results agree with the model of the $Pl^{A1}$ alloantigen recently proposed by Newman [Newman, *Thromb Haemostas*, 66:111 (1991). Furthermore, as suggested by biochemical studies [Newman et al., *Mol. Immunol*, 22:719 (1985)], the synthesis of the $Pl^{A1}$ epitope in *E. coli* proves that it does not depend on glycosylation. The ability to produce small recombinant mimics of the $Pl^{A1}$ and $Pl^{A2}$ epitopes in large amounts permits the development of simple detection assays for alloantibodies to those epitopes and platelet typing.

B. Polypeptides that Immunologically Mimic the $Pl^{A1}$ and $Pl^{A2}$ Epitopes Platelets express glycoproteins on the surface of their plasma membranes. One of those glycoproteins is an 84.5 kilodalton mature glycoprotein designated GPIIIa.

The present invention relates to an isolated polypeptides that immunologically mimic binding regions (epitopes or determinants) of the native platelet GPIIIa $Pl^{A1}$ and $Pl^{A2}$ epitopes. As used herein, the term "native" means the primary, secondary and tertiary structure of a $Pl^A$ determinant expressed on platelets.

GPIIIa is an alloantigen; i.e., different individuals express different forms of GPIIIa. The alloantigenic determinants of interest herein are denominated $Pl^A$.

One form of GPIIIa has a leucine (Leu) residue at amino acid residue position 33 from the amino-terminus of the mature glycoprotein. The antigenic determinant of that form of GPIIIa is designated the $Pl^{A1}$ determinant.

A second alloantigenic form of expressed GPIIIa has a proline (Pro) residue in place of the Leu residue at position 33. The alloantigenic determinant of that second form of GPIIIa is designated the $Pl^{A2}$ determinant.

Thus, in one embodiment, a polypeptide is contemplated that immunologically mimics a native $Pl^{A1}$ or $Pl^{A2}$ determinant. A polypeptide of the invention immunoreacts with anti-native $Pl^{A1}$ or $Pl^{A2}$ antibodies, but not with both. Thus, a contemplated polypeptide has a primary, secondary and tertiary structure sufficiently similar to that of a native $Pl^A$ epitope to immunologically mimic; i.e., immunoreact with antibodies that immunoreact with, the native epitope. A contemplated isolated polypeptide is thus said to exhibit one or the other of the native $Pl^A$ epitopes (determinants). The preparation of a suitable human antibody composition is discussed hereinafter.

A contemplated polypeptide that immunologically mimics the native $Pl^{A1}$ or $Pl^{A2}$ determinant comprises an amino acid residue sequence identical to, or conservatively substituted from (as described hereinafter), a $Pl^A$-containing portion of human platelet GPIIIa amino acid residue sequence. A contemplated polypeptide comprises a "truncated" amino acid residue sequence of GPIIIa from amino acid residue position 1 up through about position 266, and includes an amino acid residue sequence that defines an antibody-binding region (epitope) of a native $Pl^{A1}$ or $Pl^{A2}$ determinant. A contemplated polypeptide contains a sequence of about 65 to about 266 amino acid residues of the GPIIIa sequence. A particularly preferred polypeptide includes about 65 amino acid residues of the mature GPIIIa sequence; i.e., from positions 1 through 65 of GPIIIa, but can also include the sequence of the GPIIIa signal peptide that contains 26 residues at the amino-terminus; i.e., a polypeptide can include residues beginning at amino acid residue position –26.

A contemplated polypeptide can also include an immunologically "inert" spacing (linking) amino acid residue sequence, such as a β-galactosidase sequence (about 1200 residues), maltose binding protein (MBP) sequence (about 105 residues) or the a peptide of the product of the lacza gene (about 105 residues), as long as the immunologically inert sequence does not substantially interfere with the immunological binding properties of the polypeptide; i.e., as immunologically inert, as described herein. Additional "vector-induced" amino acid residues can also be present at one or both termini of a contemplated polypeptide as is discussed hereinafter.

A preferred polypeptide immunologically mimics a $Pl^A$ determinant, contains 65 residues through about 266 residues of GPIIIa and includes the amino acid residue sequence of a $Pl^{A1}$ or $Pl^{A2}$ determinant that is present in GPIIIa from amino acid residue position 1 through postion 65 of the mature proteins.

A preferred polypeptide that includes the amino acid residue sequence of the $Pl^{A1}$ determinant is shown in SEQ ID NO:7. The present invention also contemplates polypeptides containing 65 up through about 266 residues that include the amino acid residue sequence of SEQ ID NO:7, and whose remaining residues define an amino acid residue sequence of GPIIIa.

Exemplary such isolated polypeptides include the amino acid residue sequences shown in SEQ ID NO:3, SEQ ID NO:11, SEQ ID NO:13, SEQ ID NO:15, SEQ ID NO:17 and SEQ ID NO:19.

A preferred polypeptide that includes the amino acid residue sequence of the Pl$^{A2}$ determinant is shown in SEQ ID NO:9. The present invention also contemplates polypeptides containing 65 up through about 266 residues of GPIIIa that include the amino acid residue sequence of SEQ ID NO:9.

Exemplary such isolated polypeptides include the amino acid residue sequence shown in SEQ ID NO:5, SEQ ID NO:21, SEQ ID NO:23, SEQ ID NO:25, SEQ ID NO:27 and SEQ ID NO:29.

Preferably, a contemplated polypeptide of the invention is recombinantly expressed in a procaryotic host cell such as *Escherichia coli* (*E. coli*). Thus, a preferred polypeptide, which immunologically mimics the native Pl$^{A1}$ or Pl$^{A2}$ determinant, is expressed by *E. coli* transformed with a vector encoding the polypeptide. A preferred polypeptide in this regard is expressed by *E. coli* transformed with an expression vector containing the DNA segment shown in SEQ ID NO:6, which encodes the polypeptide of SEQ ID NO:7. Another preferred polypeptide is expressed by *E. coli* transformed an expression vector that contains the DNA segment shown in SEQ ID NO:8, which DNA segment encodes the polypeptide of SEQ ID NO:9. These and other expression vectors are discussed in greater detail hereinafter.

Another aspect of the present invention is a fusion polypeptide that immunologically mimics native Pl$^{A1}$ or Pl$^{A2}$ determinant. As is discussed elsewhere, a recombinant polypeptide that immunologically mimics the Pl$^{A1}$ or Pl$^{A2}$ determinant can also be expressed operatively linked to all or part of the amino acid sequence of another immunologically inert protein, such as β-galactosidase or maltose binding protein, and therefore also be a fusion polypeptide.

A subject polypeptide referred to herein as a fusion polypeptide comprises a first amino acid residue sequence that includes an amino acid residue sequence and tertiary structure of a native Pl$^{A1}$ or Pl$^{A2}$ determinant operatively linked to a second amino acid residue sequence that includes an amino acid residue sequence of all or part of an immunologically inert protein. An amino acid residue sequence is said to be "operatively linked" to a second amino acid residue sequence when the sequences are joined by one or more covalent bonds, as by a direct peptide bond or by an intervening peptide-bonded linking amino acid residue sequence. Usually, the first and second amino acid residue sequences are linked together via a peptide-bonded third amino acid residue sequence of one or more residues that are vector induced.

A preferred Pl$^{A1}$ fusion polypeptide comprises an amino acid residue sequence of a Pl$^{A1}$ determinant operatively linked to the carboxy-terminus of an amino acid residue sequence of all or part of an immunologically inert protein. The length of the fusion polypeptide is determined by the lengths of its respective Pl$^{A1}$ determinants, immunologically inert proteins, and, optionally, additional vector-induced linking amino acid residue sequences that can be present.

One preferred fusion polypeptide contains a portion of the β-galactosidase protein at the amino-terminus of a Pl$^A$ antigen. A particular, contemplated fusion polypeptide is the expression product of *E. coli* transformed with a recombinant DNA molecule comprising λgt22 phage vector (available from Promega) operatively ligated in frame to a Pl$^A$-encoding DNA segment, whose expressed DNA encodes a contemplated polypeptide as discussed before.

Another preferred fusion polypeptide is a fusion protein in which maltose binding protein (MBP) is fused to the amino-terminus of a contemplated polypeptide. A MBP-containing fusion protein can be expressed using a recombinant DNA molecule comprising a Pl$^A$-encoding DNA sequence operatively ligated in frame to a MAL™c2 or MAL™p2 plasmid vector (available from New England Biolabs). A fusion protein expressed from vectors MAL™p2 or MAL™c2 can be reacted with proteolytic blood factor Xa to remove the MBP portion to provide a lower molecular weight Pl$^A$ determinant-containing polypeptide of the invention.

Ligation of any of the isolated DNA sequences of the invention discussed hereinafter into one or the other of the above or other expression vectors discussed herein followed by appropriate host transformation results in expression of a contemplated fusion polypeptide.

Exemplary vector-induced linking sequences are formed by expression of nucleotide sequences that are utilized for restriction endonuclease cleavage of DNA molecules used to construct the recombinant molecules that express a contemplated fusion polypeptide. Thus, for example, an exemplary Pl$^{A1}$-encoding DNA sequence discussed hereinafter was flanked by Sal I restriction enzyme recognition sites and cloned into the Sal I site of λgt22. That Sal I site was flanked by Eco RI and Not I sites in the vector. Thus, the expressed fusion polypeptide contained amino acid residues expressed from those restriction sites in addition to amino acid residues of GPIIIa.

It should be apparent to any worker skilled in molecular biology that substantially any polypeptide can be used as a linking sequence so long as it is immunologically inert, as described hereinafter, and so long as it is free of residues such as cysteines and residues such as tryptophans, phenylalanines and the like that can cause insolubilization (non-dispersibility in the absence of SDS) of the expressed material or otherwise inhibit its immunoreactivity. A linking sequence, also sometimes referred to herein as a spacing sequence, can contain one residue up through about 1200 residues as is the case when a fusion polypeptide or fusion protein is expressed linked to the carboxy-terminus of β-galactosidase.

Typically a subject polypeptide, including a fusion polypeptide, is not glycosylated; i.e., as when it is expressed by a prokaryotic host such as *E. coli*. However, a polypeptide of the invention can be eukaryotically produced, in which case it may be glycosylated. Also, a subject polypeptide can incorporate a variety of changes, such as insertions, deletions, and conservative substitutions of amino acid residues as can be present in allelic variants, as long as the resulting molecule exhibits the desired properties. The "desired properties" as referred to herein include that the modified polypeptide has the same or similar immunoreactive properties as those for the unaltered polypeptide, as described hereinbefore.

When an instant polypeptide incorporates a conservative substitution in an amino acid residue sequence, the substituted amino acid residue is replaced by another, biologically similar amino acid residue such that the resulting polypeptide has an amino acid residue sequence that is compositionally different from the unsubstituted amino acid residue sequence. Some contemplated examples of conservative substitutions include substitution of a hydrophobic residue such as isoleucine, valine, leucine or methionine for another hydrophobic residue. Also, a polar residue such as arginine, lysine, glutamic acid, aspartic acid, glutamine, asparagine, and the like, can be conservatively substituted for another member of this group.

Still another aspect of a polypeptide incorporating conservative substitutions occurs when a substituted amino acid residue replaces an unsubstituted parent amino acid residue. Examples of substituted amino acids can be found at 37

C.F.R. §1.822(b)(4), which species are incorporated herein by reference. When a subject polypeptide has an amino acid residue sequence corresponding to the sequence for a native apoprotein, but for one or more conservative substitutions, preferably no more than about 40 percent, and more preferably no more than about 20 percent, of the amino acid residues of the native apoprotein are substituted in the polypeptide.

As is well-known, the presence of a proline residue in a protein or polypeptide causes a kink in the sequence that can lead to a difference in not only the primary structure, but also the secondary and tertiary structures. Indeed, the leucine$^{33}$/proline$^{33}$ replacement in GPIIIa results in the differences between the Pl$^{A1}$ and Pl$^{A2}$ alloantigenic determinants. As such, a proline residue replaced for another residue is not a conservative substitution.

A polypeptide of the present invention can be synthesized by any of the peptide synthetic techniques known to those skilled in the art. A summary of some of the techniques available can be found in J. M. Stuard and J. D. Young, "Solid Phase Peptide Synthesis", W. H. Freeman, Co., San Francisco (1969), J. Meinhofer, "Hormonal Proteins and Peptides" Vol. 2, pp. 46, Academic Press (New York) 1983, and U.S. Pat. No. 4,631,211, which description is incorporated herein by reference. These techniques usually employ a solid phase technique such as that described in Merrifield, *JACS*, 85:2149 (1963). Alternatively, a subject polypeptide can be prepared by direct coupling of two smaller polypeptides, e.g., via a peptide linkage or disulfide bridge.

Preferably, however, because of the presence of the seven cysteine residues in a contemplated polypeptide, a subject polypeptide is synthesized by recombinant DNA techniques. Such recombinant techniques are also favored especially when the desired polypeptide is relatively long, e.g., more than about 50 residues in length, as is the case here. When recombinant DNA techniques are employed to prepare a subject polypeptide, a DNA segment coding for the desired polypeptide or precursor to the polypeptide is ligated to a preselected vector for subsequent expression.

A preferred subject polypeptide is expressed by *E. coli*. Thus, a conservatively substituted polypeptide incorporating any post-translation modifications effected by *E. coli*, cells is also contemplated. Accordingly, a subject polypeptide can be expressed by *E. coli*, transformed with recombinant molecule containing a vector such as phage λgt22 or MAL™c2 or MAL™p2.

C. DNA Segments

A DNA segment of the invention (a contemplated DNA segment) encodes a before-described subject polypeptide. A DNA segment is contemplated to be a discrete, "isolated" chemical species available for manipulation, as when generated by the polymerase chain reaction (PCR), as described below. All DNA segments discussed herein have both 5' and 3' ends.

Alternatively, an isolated, subject DNA segment can be operatively ligated to a vector, as when it is to be cloned or subsequently expressed in a suitable host. The DNA segment is "operatively ligated" to a vector when it is covalently bonded in frame to the vector for expression of a subject polypeptide or fusion polypeptide, as is well known. Additionally, when the DNA segment is operatively ligated to an expression vector, a promoter sequence is present so that expression of the DNA segment is under the control of the promoter sequence. Vectors containing an operatively ligated subject DNA segment are discussed in greater detail hereinafter.

A preferred isolated DNA segment comprises a nucleotide sequence of at least 195 base pairs (bp) encoding a subject polypeptide, such as the amino acid residue sequence of SEQ ID NO:7 or SEQ ID NO:9. The nucleotide sequence encoding the Pl$^{A1}$ or Pl$^{A2}$ determinant amino acid residue sequence can include up through about 800 nucleotide base pairs of the GPIIIa sequence as shown in SEQ ID NO:2 or SEQ ID NO:4.

In one embodiment, an isolated DNA molecule of this invention contains about 195 to about 800 nucleotide base pairs (bp) that encodes an amino acid residue sequence of GPIIIa that includes the Pl$^{A1}$ determinant. Preferably, that amino acid residue sequence of GPIIIa is SEQ ID NO:3, SEQ ID NO:7, SEQ ID NO:11, SEQ ID NO:13, SEQ ID NO:15, SEQ ID NO:17 or SEQ ID NO:19. Isolated DNA molecules that encode those amino acid residue sequences are shown in SEQ ID NO:2, SEQ ID NO:6, SEQ ID NO:10, SEQ ID NO:12, SEQ ID NO:14, SEQ ID NO:16 and SEQ ID NO:18, respectively.

In another embodiment, an isolated DNA molecule of this invention contains about 195 to about 800 nucleotide base pairs that encodes an amino acid residue sequence of GPIIIa that includes the Pl$^{A2}$ determinant. Preferably, that amino acid residue sequence of GPIIIa is SEQ ID NO:5, SEQ ID NO:9, SEQ ID NO:21, SEQ ID NO:23, SEQ ID NO:25, SEQ ID NO:27 or SEQ ID NO:29. Isolated DNA molecules that encode those amino acid residue sequences are shown in SEQ ID NO:4, SEQ ID NO:8, SEQ ID NO:20, SEQ ID NO:22, SEQ ID NO:24, SEQ ID NO:26 and SEQ ID NO:28, respectively.

A subject isolated DNA segment or that segment ligated into a vector as a recombinant DNA molecule discussed hereinafter can also include codons that encode amino acid residues other than those of a Pl$^{A1}$ or Pl$^{A2}$ determinant sequence; i.e., a vector-induced residue or sequence. Those other codons and encoded amino acid residues of an expressed polypeptide constitute the previously discussed spacing (linking) sequence previously discussed.

Thus, a contemplated polypeptide can be encoded by a subject isolated DNA segment. Frequently, as in the case of an expressed fusion polypeptide, the a portion of a contemplated polypeptide is contributed by the vector, although by appropriate selection of vectors and restriction sites, an isolated DNA segment of the invention can also encode a desired polypeptide without the spacing amino residue sequence.

The total length of an isolated DNA segment of the invention is mostly a matter of choice once, at least, a before-mentioned Pl$^{A1}$ or Pl$^{A2}$ determinant encoding sequence is present. For example, one to several thousand base pairs can be present downstream of the expression stop codon. Similarly, one to several thousand or more base pairs can be present upstream from the Pl$^{A1}$ or Pl$^{A2}$ determinant expression start codon, so long as the expression frame is maintained, as where a subject DNA segment includes codons for a Pl$^{A1}$ or Pl$^{A2}$ determinant as well as a portion of the β-gal gene and the regulatory sequences for the β-gal gene.

An RNA segment equivalent (complementary) to a DNA segment described above is also contemplated. In this embodiment, an RNA segment can be ligated to an RNA vector, e.g., viral RNA, as is well known.

A subject DNA segment can be readily synthesized by chemical techniques, e.g., by the well-known phosphotriester method [Matteuci et al., *JACS*, 103:3185 (1981)]. By chemically synthesizing the DNA segments, any desired substitution, insertion or deletion of an amino acid residue or sequence from a template polypeptide can be readily provided by making the corresponding change in the nucleotide sequence of the DNA segment.

In addition to synthetic chemical techniques, a DNA segment of the invention can be produced by enzymatic techniques. Thus, restriction enzymes, which cleave DNA molecules at predefined recognition sequences, can be used to isolate DNA fragments from larger DNA molecules that encode a subject polypeptide. Typically, DNA fragments produced in this manner have cohesive, "overhanging" termini, whereby single-stranded nucleotide sequences extend beyond the double-stranded region of the molecule. The presence of such cohesive termini is often preferred over blunt-ended DNA molecules, although blunt-ended DNA can be used as can fragments having one blunt end and one overhanging end. A relatively less specific enzyme such as DNAase I that typically provides blunt-ended termini can also be used, and was was herein. The isolated DNA fragments can then be operatively ligated (cloned) into a suitable vector, thereby incorporating the subject DNA segment into the vector.

Whenever an RNA segment coding for a subject polypeptide is used, an RNA molecule including the RNA segment is transcribed into complementary DNA (cDNA) via a reverse transcriptase. The cDNA molecule can then be ligated to an expression vector which can be transformed in a suitable host to give the desired subject polypeptide.

A DNA segment coding for an above-described amino acid residue sequence can be provided with start and stop codons, or one or both of the start and stop codons can be provided by the larger DNA molecule, e.g., vector, operatively ligated to the DNA segment. A desired polypeptide of the invention can be prepared by judicious placement of the start and stop codons. For instance, a nucleotide sequence can be provided at one or both of the 3' and 5' ends of the DNA segment so that a polypeptide is expressed which is larger than an epitope amino acid residue sequence discussed before by inclusion of an N-terminal or C-terminal amino acid residue sequence. Additionally, it is contemplated that regulator, promoter and operator loci can be provided at the 5' end of a subject DNA segment as desired.

In addition to standard chemical or enzymatic synthetic techniques, an instant DNA segment can be generated using a polymerase chain reaction (PCR) protocol. In PCR, a specific polynucleic acid target is transcribed by a reaction in which a primer molecule complementary to a particular section of a nucleic acid template is used to form an extension product of the primer including a nucleic acid region complementary to the target. After separation of template and extended primer, each primer extension product acts as a template and specifically anneals with a complementary primer molecule. The resulting primed template acts as a substrate for further extension reactions. These steps are repeated, preferably using an automated cycling procedure, thereby exponentially amplifying the initial polynucleic acid target to which the primer hybridizes. Procedures for conducting PCR have been extensively described, see, e.g., U.S. Pat. Nos. 4,683,195 and 4,683,202, which descriptions are incorporated herein by reference.

As a target DNA segment frequently is present only in very small quantities, PCR affords sufficient amplification of the target DNA segment to permit efficient cloning and expression of the targeted segment.

As PCR employs forward and reverse single stranded oligonucleotide primer molecules to initiate the polymerization reaction at each amplification stage, forward and reverse primer molecules complementary to at least a portion of the target DNA segment are contemplated. Also contemplated are primer molecules having a nucleotide sequence that defines a recognition sequence of a preselected restriction enzyme which flanks the region of the primer molecule complementary to the target DNA segment.

The primer must be sufficiently long to prime the synthesis of extension products in the presence of the agents for polymerization. The exact lengths of the primers depend on many factors, including temperature and the source of primer. For example, depending on the complexity of the template sequence, a polynucleotide primer typically contains 15 to 25 or more nucleotides, although it can contain fewer nucleotides. As few as 8 nucleotides in a polynucleotide primer have been reported as effective for use [Studier et al, *Proc. Natl. Acad. Sci. USA*, 86:6917–21 (1989)]. Short primer molecules generally require lower temperatures to form sufficiently stable hybridization complexes with template to initiate primer extension.

The primers used are selected to be substantially complementary to the strands of each sequence to be amplified. Accordingly, the primer contains a nucleotide sequence sufficiently complementary to non-randomly hybridize with its respective template strand. Therefore, the hybridizing region of the primer sequence may not be exactly complementary with the template.

For example, a non-complementary polynucleotide can be attached to the 5' end of the primer, with the remainder of the primer sequence being substantially complementary to the strand. Such noncomplementary polynucleotide can code for a site for protein binding or permit adjustment of the reading frame of the codons. Also, a noncomplementary base can be interspersed in the primer, provided the primer sequence has sufficient complementarity with the sequence of the template strand to allow non-random hybridization to take place under hybridizing conditions, e.g., as when an inosine base is used for nonspecific coding. Primers having as little as a three-nucleotide exact match at the 3' end of the primer can be capable of specifically initiating primer extension products [Sommer, et al., *Nuc. Acid Res.*, 17:6749 (1989)].

Preferably, the primer is provided in single-stranded form for maximum efficiency, but it can be double-stranded. If a double-stranded primer is used, the primer is first melted to separate its strands before being used to prepare extension products. Preferably, the primer is a polydeoxyribonucleotide.

Primers can be prepared by a variety of methods including de novo chemical synthesis and derivation of nucleic acid fragments from native nucleic acid sequences such as genes, alleles, introns, and codons of a genome, plasmid, or vector. Fragments can be obtained by such methods as restriction endonuclease limit digest of larger double-stranded nucleic acids and polymeric synthesis using a polymerase and a nucleic acid template. De novo chemical synthesis of a polynucleotide is generally preferred when a native DNA sequence coding for a subject polypeptide is known and can be conducted using any suitable method, such as the well-known phosphotriester or phosphodiester methods. See, for example, Narang et al, *Meth. Enzymol.*, 68:90, (1979); Itakura et al, *Ann. Rev. Biochem.*, 53:323–56 (1989); Brown et al, *Meth. Enzymol.*, 68:109, (1979); and U.S. Pat. No. 4,356,270, which description is incorporated herein by reference.

Derivation of a primer molecule from nucleic acids typically involves introducing a nucleic acid into an appropriate host as with a cloning vector, replication of the vector to increase the amount of cloned nucleic acid, followed by isolation of fragments or subfragments of the cloned nucleic acids. A description of techniques for subcloning nucleic acid fragments is found in Maniatis et al, *Molecular Cloning: A Laboratory Manual*, Cold Spring Harbor Laboratory, pp 390–401 (1982); and U.S. Pat. Nos. 4,416,988 and 4,403,036, which descriptions are incorporated herein by reference.

Template nucleic acid sequences to be hybridized in the present methods can be present in any nucleic acid-containing sample so long as the sample is in a form, with respect to purity and concentration, compatible with nucleic acid hybridization reaction. Isolation of nucleic acids to a degree suitable for hybridization is generally known and can be accomplished by a variety of means. See, for example, Maniatis et al, *Molecular Cloning: A Laboratory Manual*, Cold Spring Harbor Laboratory (1982); and Ausubel et al, *Current Protocols in Molecular Biology*, John Wiley and Sons (1987).

The hybridization reaction is carried out under predefined conditions that permit a primer to hybridize to its complementary nucleic acid template. "Hybridizing conditions," and grammatical equivalents thereof, as used herein, refer to the set of incubation time periods, temperature and pH parameters that permit the primer to anneal with the template sequence, typically to form a nucleic acid duplex. Such hybridization conditions depend on factors such as the length of the primer to be hybridized, the degree of complementarity between the primer and the template, the guanosine and cytidine content of the polynucleotide, the stringency of hybridization desired, and the presence of salts or additional reagents in the hybridization reaction admixture that may affect the kinetics of hybridization. Methods for optimizing hybridization conditions for a given hybridization reaction admixture are well known in the art but typically the hybridizing conditions involve solutions buffered to pH values between 4 and 9 at temperatures from 18° C. to 75° C., preferably about 37° C. through about 65° C., more preferably about 54° C., for time periods from 0.5 seconds to 24 hours, preferably about two minutes.

Hybridization can be carried out in a homogeneous or heterogeneous format as is well known. The homogeneous hybridization reaction occurs entirely in solution, in which both the primer and template sequences to be hybridized are present in soluble forms in solution. A heterogeneous reaction involves the use of a matrix that is insoluble in the reaction medium to which either the primer or template is bound. Also contemplated are the homogeneous hybridization reactions such as are conducted in the reverse transcription of isolated mRNA or viral RNA to form cDNA, dideoxy sequencing and other procedures using primer extension reactions in which primer hybridization is a first step.

Where the nucleic acid-containing a template sequence is in a double-stranded (ds) form, it is preferably denatured as by heating or alkali treatment prior to conducting the hybridization reaction. The denaturation of the dsDNA can be carried out prior to admixture with a primer to be hybridized or can be carried out after admixture of the dsDNA with the primer. Where the primer itself is provided as a double-stranded molecule, it can also be denatured prior to admixture or it can be denatured concurrently with the template-containing dsDNA.

The primer extension reaction is performed using any suitable method. Preferably, a molar excess (for genomic nucleic acid, usually about $10^6$:1 primer:template) of the primer is admixed to the buffer containing the template strand. A large molar excess is preferred to improve the efficiency of the process. For polynucleotide primers of about 20 to 25 nucleotides in length, a typical ratio is in the range of 50 ng to 1 μg, preferably 250 ng, of primer per 100 ng to 500 ng of mammalian genomic DNA or per 10 to 50 ng of plasmid DNA.

Deoxyribonucleotide triphosphates (dNTPs) DATP, dCTP, dGTP, and dTTP are also admixed to the primer extension reaction admixture in amounts adequate to support the synthesis of primer extension products. The amounts used are readily determined by the skilled practitioner.

In a typical primer extension reaction, the hybridization admixture is heated through about 90–100° C. for about one to 10 minutes, preferably from one to four minutes. After this heating period the solution is allowed to cool to room temperature to permit primer/template hybridization. To the cooled mixture is added an appropriate agent for inducing or catalyzing the primer extension reaction. The synthesis reaction can occur at from room temperature up to a temperature above which the inducing agent no longer functions efficiently. Thus, for example, if DNA polymerase is used as the inducing agent, a suitable temperature is generally no greater than about 40° C. unless the polymerase is heat-stable.

The inducing agent can be any compound or system that effects synthesis of primer extension products. Suitable enzymes for this purpose include, for example, *E. coli*, DNA polymerase I, Klenow fragment of *E. coli*, DNA polymerase I, T4 DNA polymerase, T7 DNA polymerase, recombinant modified T7 DNA polymerase, and other DNA polymerases, reverse transcriptases, and other enzymes that facilitate the primer extension reaction.

Heat-stable (thermophilic) DNA polymerases are particularly preferred in this regard as they are thermally stable in an automated temperature cycling PCR format. Representative heat-stable polymerases are the DNA polymerases isolated from *Bacillus stearothermophilus* (Bio-Rad, Richmond, Calif.), *Thermus thermophilus* (FINZYME, ATCC #27634), Thermus species (ATCC #31674), *Thermus aquaticus* strain TV 1151B (ATCC #25105), *Sulfolobus acidocaldarius*, described by Bukhrashuili et al, *Biochem. Biophys. Acta*, 1008:102 (1989) and by Elie et al, *Biochem. Biophys. Actz*, 951:261 (1988), *Thermus filiformis* (ATCC #43280), the polymerase isolated from *Thermus flavus* (Molecular Biology Resources; Milwaukee, Wis.), and "Vent" polymerases (New England Biolabs, Beverly, Mass.). Particularly preferred are Taq DNA polymerase, available from a variety of sources including Perkin Elmer Cetus, (Norwalk, Conn.), Promega (Madison, Wis.) and Stratagene (La Jolla, Calif.), and AMPLITAQ DNA polymerase, a recombinant Taq DNA polymerase available from Perkin-Elmer Cetus.

PCR is typically carried out by cycling the following steps on a reaction admixture: (1) heating to form denatured single-stranded templates and primers, (2) cooling to permit hybridization of primer to template, and (3) maintenance at predefined conditions to permit formation of primer extension products. Methods and systems for amplifying a specific nucleic acid sequence by PCR are described in U.S. Pat. Nos. 4,683,195 and 4,683,202, which are incorporated herein by reference, and in *PCR Technology*, Erlich, ed., Stockton Press (1989); Faloona et al, *Methods in Enzymol.*, 155:335 (1987); and *Polymerase Chain Reaction*, Erlich et al, eds., Cold Spring Harbor Laboratory Press (1989).

Detection of amplified nucleic acid product can employ any of a variety of well known techniques. In a preferred embodiment, the amplified product is separated on the basis of molecular weight by gel electrophoresis and the separated products are visualized with nucleic acid specific stains. Although numerous nucleic acid specific stains exist and would be suitable to visualize the electrophoretically separated nucleic acids, ethidium bromide is preferred.

Alternative methods for detecting the amplified nucleic acid product include hybridization-based detection means that use a labeled oligonucleotide probe capable of hybridizing to the amplified product. Exemplary of such detection means include the Southern blot analysis, ribonuclease protection analysis using in vitro labeled polyribonucleotide probes, and similar methods for detecting nucleic acids having specific nucleotide sequences. See, for example, Ausubel et al., *Current Protocols in Molecular Biology*, John Wiley & Sons, 1987.

In another approach for detecting the presence of a specific nucleic acid sequence, the deoxyribonucleotide triphosphates (dNTPs) used in the primer extension reaction include a label or indicating group that renders a primer extension product detectable. Typically such labels include radioactive atoms, chemically modified nucleotide bases, and the like. Suitable radioactive labels include $^3$H, $^{14}$C, $^{32}$P, and $^{35}$S, and the like.

Alternatives to radioactively labeled dNTPs are dNTPs modified chemically to contain metal complexing agents, biotin-containing groups, fluorescent compounds, and the like. A useful metal complexing agent is a lanthanide chelate compound formed by a fluorescent lanthanide metal and beta-diketonate ligands. The lanthanide binds to the nucleic acid so that a fluorescent lanthanide/nucleic acid complex is formed. See U.S. Pat. Nos. 4,374,120, 4,569,790 and published International Patent Application Nos. EP0139675 and WO87/02708, which descriptions are incorporated herein by reference.

Biotin or acridine ester-labeled oligonucleotides and their use in polynucleotides have been described. See U.S. Pat. No. 4,707,404, published International Patent Application EP0212951 and European Patent No. 0087636. Useful fluorescent markers for oligonucleotides include fluorescein, rhodamine, Texas Red, NBD and the like.

Techniques for separating non-hybridized labeled probes from hybridized probes are well known, and typically involve the separation of single stranded from double stranded nucleic acids on the basis of their chemical properties. Frequently, a heterogeneous separation format is used in which non-hybridized probe is separated as by washing from the labeled DNA duplexes bound to an insoluble matrix. Exemplary of this technique are Southern blots in which the matrix is a nitrocellulose sheet and the label is $^{32}$P [Southern, *J. Mol. Biol.*, 98:503 (1975)].

D. Recombinant DNA Molecules

A recombinant DNA molecule comprising a vector operatively ligated to an above-described DNA segment (an exogenous DNA segment) is also contemplated. The recombinant DNA molecule (DNA construct) can facilitate amplification and/or expression of a subject DNA segment coding for a polypeptide of the invention.

A contemplated recombinant DNA molecule incorporates a before-discussed isolated DNA segment coding for an amino acid residue sequence of a native $Pl^{A1}$ or $Pl^{A2}$ determinant. Preferably, the DNA segment is selected from the group consisting of SEQ ID NO's:2, 4, 6, 8, 10, 12, 14, 16, 18, 20, 22, 24, 26 and 28.

A particularly preferred recombinant DNA molecule, which is replicable upon transformation in a suitable host cell, contains the subject DNA segment of SEQ ID NO:10 that encodes the amino acid residue sequence of the $Pl^{A1}$ determinant and contains a nucleotide base sequence that encodes the leader amino acid residue sequence of GPIIIa. Another preferred DNA segment, shown in SEQ ID NO:20, encodes the $Pl^{A2}$ determinant. Preferably, the DNA construct contains a nucleotide sequence of about 195 up through about 800 base pairs encoding a subject polypeptide.

Typically, a recombinant DNA molecule of the present invention contains a DNA sequence coding for an immunologically "inert" linking peptide sequence fused to an above-described $Pl^{A1}$ or $Pl^{A2}$ determinant. An exemplary sequence in this regard codes for a β-galactosidase or MBP moiety. Such a recombinant DNA molecule can be obtained by inserting a subject DNA segment in frame into a vector containing a gene encoding the β-galactosidase or MBP protein or polypeptide.

A contemplated recombinant DNA molecule (vector) can be circularized or linearized.

A further aspect of the invention relates to a recombinant DNA molecule that includes an expression vector that is operatively ligated to a before-described DNA segment that encodes a fusion polypeptide. The vector molecule permits amplification and expression of a fusion polypeptide that includes a before-described amino acid residue sequence of a $Pl^{A1}$ or $Pl^{A2}$ determinant in native form operatively linked to a before-described, amino acid residue sequence of an immunologically inert protein.

Accordingly, an exemplary vector encoding a subject fusion polypeptide comprises:

(a) a first nucleotide sequence containing about 3600 nucleotides that encodes an amino acid residue sequence including an amino acid residue sequence of the whole or part of an immunologically inert protein such as β-galactosidase or MBP, with the second nucleotide sequence operatively ligated to the first nucleotide sequence; and (b) a second nucleotide sequence containing about 195 to about 800 nucleotides that encodes an amino acid residue sequence of GPIIIa that incldues the amino acid residue sequence of the native $Pl^{A1}$ or $Pl^{A2}$ determinant.

Preferably, the second nucleotide sequence contains about 275 nucleotides. Such a nucleotide sequence that encodes an amino acid residue sequence of GPIIIa that includes the amino acid residue sequence of the native $Pl^{A1}$ determinant is shown in SEQ ID NO:10. A nucleotide sequence that encodes an amino acid residue sequence of GPIIIa that includes the amino acid residue sequence of the native $Pl^{A2}$ determinant is shown in SEQ ID NO:20.

The choice of vector to which a DNA segment of the present invention is operatively ligated to form a contemplated recombinant DNA molecule depends on the functional properties desired, e.g., efficiency of transcription, efficiency of expression within the selected transformation host cell, location of restriction sites (as when PCR products are directly cloned into the vector), and the like. However, a vector of the present invention is at least capable of directing the replication of a DNA segment coding for a subject polypeptide.

Preferably, a chosen vector includes a prokaryotic replicon; i.e., a DNA sequence having the ability to direct autonomous replication and maintenance of the recombinant DNA molecule extrachromosomally in a prokaryotic host cell transformed therewith. Such replicons are well known in the art. In addition, a vector that includes a prokaryotic replicon preferably also includes a drug resistance gene so that hosts transformed with a vector can be readily screened. Typical bacterial drug resistance genes are those that confer resistance to ampicillin or tetracycline. The use of β-galactosidase as a screening means based on sugar metabolism is also contemplated.

Vectors that include a prokaryotic replicon preferably include a prokaryotic promoter capable of directing the transcription of the instant polypeptide genes. A promoter is an expression control element formed by a DNA sequence that promotes binding of RNA polymerase and transcription of single-stranded DNA into messenger RNA (mRNA)

molecules. Promoter sequences compatible with bacterial hosts, such as a tac promoter, are typically provided in plasmid vectors having convenient restriction sites for insertion of a DNA segment of the present invention. Typical of such vector plasmids are pUC8, pUC9, pBR322 and pBR329 available from Biorad Laboratories, (Richmond, Calif.); pPL, pUR, pKK223 available from Pharmacia (Piscataway, N.J.); MAL c2 and MAL p2 available from New England Biolabs (Beverly Mass.); and λgt22 available from Promega Corp. (Madison, Wis.). The λgt22 vector is preferred.

Expression vectors compatible with eukaryotic cells, preferably those compatible with vertebrate cells, can also be used to form a recombinant DNA molecule described before. Eukaryotic cell expression vectors are well known in the art and are available from several commercial sources. Typically, such vectors are provided with convenient restriction sites for insertion of the desired DNA segment. Typical of such vectors are pSVL and pKSV-10 (Pharmacia), pBPV-1pML2d (International Biotechnologies, Inc.), and PTDT1 (ATCC, #31255). A preferred drug resistance marker for use in vectors compatible with eukaryotic cells is the neomycin phosphotransferase (neo) gene. [Southern et al., *J. Mol. Appl. Genet.*, 1:327–341 (1982)].

Retroviral vectors that express a recombinant DNA of the present invention are also contemplated. The construction and use of retroviral vectors for expressing desired DNA molecules have been described. See, e.g., Sorge, et al., *Mol. Cell. Biol.*, 4:1730–37 (1984).

A number of methods are available to operatively link an instant DNA segment to a vector via complementary cohesive termini. For instance, complementary homopolymer tracts can be added to the DNA segment to be inserted and to the vector DNA. The vector and DNA segment are then hybridized by hydrogen bonding between the complementary homopolymer tails to form recombinant duplex DNA molecules. Alternatively, synthetic linkers containing one or more restriction sites can be used to join an instant DNA segment to a vector.

When a DNA segment is prepared by endonuclease restriction digestion, it can be treated with a DNA polymerase that removes protruding 3' single-stranded termini and fills in recessed 3' ends, thereby generating blunt-ended DNA segments. Blunt-ended DNA segments are incubated with a large molar excess of linker molecules in the presence of an enzyme, such as bacteriophage T4 DNA ligase, which is able to catalyze the ligation of blunt-ended DNA molecules. Thus, the products of the reaction are DNA segments covalently joined at their ends to linker sequences having restriction sites therein. The restriction sites of these DNA segments are then cleaved with the appropriate restriction enzyme and the segments ligated to an expression vector having termini compatible with those of the cleaved DNA segment. Synthetic linkers containing a variety of restriction endonuclease sites are commercially available from a number of sources including International Biotechnologies, Inc. (New Haven, Conn.).

E. Transformation and Purification

Also contemplated within the invention are cells stably transformed with a before-described recombinant DNA molecule that contains a before-described DNA segment. The host cell can be either prokaryotic or eukaryotic. Preferred prokaryotic host cells are strains of *E. coli*, e.g., the *E. coli*, strain Y1090(r⁻), Y1089(r⁻) or LE392 (available from Promega). Preferred eukaryotic host cells include yeast such as *S. cerivisiae* and mammalian cells, preferably vertebrate cells such as those from mouse, rat, goat, or primate cell lines such as Chinese hampster ovary (CHO) cells.

Transformation of a suitable host cell such as Y1090 strain *E. coli*, with a recombinant DNA molecule of the present invention is accomplished by well-known methods that typically depend on the type of vector used. With regard to transformation of prokaryotic host cells, see, e.g., Maniatis et al., *Molecular Cloning, A Laboratory Manual*, Cold Spring Harbor Laboratory, Cold Spring Harbor, N.Y. (1982). With regard to transformation of vertebrate cells with retroviral RNA vectors, see, e.g., Sorge et al., *Mol. Cell. Biol.*, 4:1730–37 (1984).

Successfully transformed cells; i.e., those stably transformed with a recombinant DNA molecule of the present invention, can be identified by well-known techniques. For example, stably transformed cells can be cloned to produce monoclonal colonies. Cells from those colonies can be harvested, lysed and their DNA content examined for the presence of the desired DNA segment using a method such as that described by Southern, *J. Mol. Biol.*, 98:503 (1975).

In addition to directly assaying for the presence of the desired DNA segment, successful transformation can be confirmed by well-known immunological methods when the transformed cells express an above-described polypeptide. In this method, samples of cells suspected of being transformed are maintained under culture in an appropriate nutrient culture medium for a time period sufficient to express the polypeptide. Those cells are harvested and assayed for a desired antigenicity using antibodies that immunoreact with (specifically bind to) a contemplated polypeptide.

Also contemplated are cultures of stably transformed host cells. Nutrient media useful for culturing transformed host cells are well known in the art and can be obtained from several commercial sources. When a mammalian host cell is employed a "serum-free" medium is preferably used.

Once stably transformed host cells are identified, those cells can be used in a method for expressing (preparing) a contemplated polypeptide by maintaining (culturing) those transformed cells under appropriate culture conditions for a time period sufficient for the cells to express the polypeptide. The expressed polypeptide is preferably isolated (recovered) from the cultured cells.

Methods for recovering an expressed protein from a culture are well-known in the art. For instance, gel filtration, gel chromatography, ultrafiltration, electrophoresis, ion exchange, affinity chromatography and related techniques can be used to isolate an expressed protein from the culture. In addition, immunochemical methods, such as immunoaffinity, immunoadsorption, and the like, can be performed using well-known methods, as exemplified by the methods described herein.

F. Antibodies and Inocula

An isolated polypeptide of the present invention can be used as an immunogen for the preparation of antibodies that immunoreact with the native GPIIIa Pl$^{A1}$ or Pl$^{A2}$ determinants. Because an isolated peptide of the present invention has substantially the same primary, secondary and tertiary structure as the native GPIIIa Pl$^{A1}$ and Pl$^{A2}$ determinants, the antibodies produced immunoreact with both the isolated polypeptide and one of the native Pl$^{A1}$ or Pl$^{A2}$ antigenic determinants, but not the other.

Antibodies of the present invention are typically produced by immunizing a host mammal with an inoculum containing a polypeptide of this invention and maintaining the host for a time period sufficient for antibodies to be raised, thereby inducing in the mammal antibody molecules having immunospecificity for the native GPIIIa Pl$^{A1}$ or Pl$^{A2}$ determinants. The antibody molecules are then collected from the mammal and isolated to the extent desired by well known techniques such as, for example, by using DEAE Sephadex to obtain the IgG fraction.

The word "inoculum" in its various grammatical forms is used herein to describe an aqueous composition containing an immunogenic amount of a polypeptide of this invention alone or as a fusion polypeptide as an active ingredient used for the preparation of antibodies immunoreactive with the native GPIIIa $Pl^{A1}$ or $Pl^{A2}$ determinants. An inoculum often includes an adjuvant to assist in antibody induction.

Isolated polypeptides or fusion polypeptides of this invention suitable for use in inocula to produce antibody molecules having immunospecificity for the native GPIIIa $Pl^{A1}$ determinants are those described hereinbefore and include the amino acid sequences of SEQ ID NO's:3, 7, 11, 13, 15, 17 and 19. Particularly preferred isolated polypeptides include amino acid residue sequences of SEQ ID NO:7 and SEQ ID NO:11.

Isolated polypeptides or fusion polypeptides of this invention suitable for use in inocula to produce antibody molecules having immunospecificity for the native GPIIIa $Pl^{A2}$ determinants are those described hereinbefore and include the amino acid sequences of SEQ ID NO's:5, 9, 21, 23, 25, 27, and 29. Particularly preferred isolated polypeptides include amino acid residue sequences of SEQ ID NO:9 and SEQ ID NO:21.

The above antibody compositions are oligoclonal.

To produce antibody molecules that immunoreact with only one of the native GPIIIa $Pl^{A1}$ or $Pl^{A2}$ determinants but not other GPIIIa or other determinants such as those to the other portion of a fusion polypeptide, immunoadsorption methods are used to remove the undesirable immunospecificities.

Immunoadsorption methods to remove immunospecificities are generally well known and typicall involve first contacting a composition containing the desired antibody molecules with a solid phase having affixed thereto one or the other of native GPIIIa $Pl^{A1}$ or $Pl^{A2}$ determinant-containing polypeptides to form an immunoadsorption admixture. The polypeptide preferably includes only amino acid residues 1 through 65 of GPIIIa so as to minimize cross-reacting with other GPIIIa epitopes.

The immunoadsorption admixture is maintained under immunoreaction conditions and for a time period sufficient for an immunocomplex to form in the solid phase; i.e., to form a solid phase-affixed immunocomplex. Thereafter, the liquid and solid phases are separated, and the solid phase is retained having the desired antibody molecules immunoadsorbed onto the solid phase. The bound antibodies of the immunocomplex are then seaprated from the complex by standard techniques.

Repeating the above separation using the other PlA antigen affixed to the solid phase provides antibodies in the liquid phase that immunoreact with one determinant but not the other.

Preferred antibody molecules are oligoclonal antibodies; i.e., antibodies that immunoreacts with a limited number of epitopes on an antigen. A preferred oligoclonal antibody composition immunoreacts with the epitope of the amino-terminal 65 amino acids of a native GPIIIa molecule; i.e., one or the other of the $Pl^{A1}$ or $Pl^{A2}$ determinants. Such oligoclonal antibodies can be prepared using the above immunoadsorption technique or by immunizing with one of the $Pl^{A}$ determinant-containing polypeptides or fusion polypeptides discussed before.

Monoclonal antibodies (Mabs) to a native $Pl^{A}$ determinant are also contemplated by the present invention. The phrase "monoclonal antibody composition" in its various grammatical forms refers to a population of antibody molecules that contain only one species of antibody combining site capable of immunoreacting with a particular antigen. The instant Mab composition thus typically displays a single binding affinity for any antigen with which it immunoreacts.

Mabs of the present invention are typically composed of antibodies produced by clones of a single cell, called a hybridoma, that secretes (produces) but one kind of antibody molecule. The hybridoma cell is formed by fusing an antibody-producing cell and a myeloma or other self-perpetuating cell line. Such antibodies were first described by Kohler and Milstein, *Nature*, 256:495–497 (1975), which description is incorporated by reference. A more recent description of monoclonal antibody preparation can be found in U.S. Pat. No. 4,818,678, whose disclosures are also incorporated by reference.

The hybridoma or other cell (below) supernates so prepared can be screened for immunoreactivity with both native GPIIIa $Pl^{A1}$ and GPIIIa $Pl^{A2}$ determinants such as the isolated polypeptides used in the inoculum to induce the antibody-producing host cell. One or more hybridoma or other cell lines that secrete antibodies that immunoreact with one determinant but not the other are then perpetuated, as by cloning.

A monoclonal antibody can also be produced by methods well known to those skilled in the art of producing chimeric antibodies. Those methods include isolating, manipulating, and expressing the nucleic acid that codes for all or part of an immunoglobulin variable region including both the portion of the variable region comprising the variable region of immunoglobulin light chain and the portion of the variable region comprising the variable region of immunoglobulin heavy chain. Methods for isolating, manipulating, and expressing the variable region coding nucleic acid in procaryotic and eucaryotic hosts are disclosed in Robinson et al., PCT Publication No. WO 89/0099; Winter et al., European Patent Publication No. 0239400; Reading, U.S. Pat. No. 4,714,681; Cabilly et al., European Patent Publication No. 0125023; Sorge et al., *Mol. Cell Biol.*, 4:1730–1737 (1984); Beher et al., *Science*, 240:1041–1043 (1988); Skerra et al., *Science*, 240:1030–1041 (1988); and Orlandi et al., *Proc. Natl. Acad. Sci. USA*, 86: 3833–3837 (1989). Typically the nucleic acid codes for all or part of an immunoglobulin variable region that binds a preselected antigen (ligand). Sources of such nucleic acid are well known to one skilled in the art and, for example, may be obtained from a hybridoma producing a monoclonal antibody that binds the preselected antigen, or the preselected antigen may be used to screen an expression library coding for a plurality of immunoglobulin variable regions, thus isolating the nucleic acid.

Also contemplated by this invention is the hybridoma cell, and cultures containing a hybridoma cell that produce a monoclonal antibody of this invention.

The antibodies so produced can be used, inter alia, in a method and system of the present invention to type platelets in a body sample or screen a blood sample.

The preparation of an inoculum that contains a peptide as an active ingredient is well understood in the art. Typically, such inocula are prepared as injectables, either as liquid solutions or suspensions. Solid forms suitable for solution in, or suspension in, liquid prior to injection may also be prepared. The preparation can also be emulsified.

The active immunogenic ingredient is dissolved, dispersed or admixed in an aqueous excipient that is pharmaceutically acceptable and compatible with the active ingredient as is well known. The phrases "pharmaceutically acceptable" or "physiologically tolerable" refer to molecular entities and compositions that typically do not produce an allergic or similar untoward reaction, and the like, when administered to a host mammal. Suitable excipients can take a wide variety of forms depending on the intended use and are, for example, aqueous solutions containing saline, phosphate buffered saline (PBS), dextrose, glycerol, ethanol, or the like and combinations thereof. In addition, if desired, the inoculum can contain minor amounts of auxiliary substances such as wetting or emulsifying agents, pH buffering agents, mineral oils, carriers or adjuvants which enhance the effectiveness of the inoculum. A preferred embodiment contains at least about 0.01 percent to about 99 percent of an isolated polypeptide or fusion polypeptide of this invention as an active ingredient, typically at a concentration of about 10 to 200 μg of active ingredient per milliliter (ml) of excipient.

An inoculum can also comprise an isolated polypeptide or fusion polypeptide of this invention linked to an antigenic carrier to facilitate the production of an immune response in the immunized mammal. Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as poly amino acids such as poly(D-lysine: D-glutamic acid), and the like.

One or more additional amino acid residues can be added to the amino- or carboxy-termini of the polypeptide to assist in binding that polypeptide to a carrier if not already present on the polypeptide. Cysteine residues added at the amino- or carboxy-termini of the peptide are particularly useful for forming polymers via disulfide bonds. However, other methods well known in the art for preparing conjugates can also be used. Exemplary additional linking procedures include the use of Michael addition reaction products, dialdehydes such as glutaraldehyde [Klipstein et al., $J.$ $Infect.$ $Dis.$, 147:318–326 (1983)] and the like, or the use of carbodiimide technology as in the use of a water-soluble carbodiimide to form amide links to the carrier.

As is also well known in the art, it is often beneficial to bind an isolated polypeptide to its carrier by means of an intermediate, linking group. As noted above, glutaraldehyde is one such linking group. However, when cysteine is used, the intermediate linking group is preferably an m-maleimidobenxoyl N-hydroxy succinimide (MBS).

Additionally, MBS can be first added to the carrier by an ester-amide interchange reaction. Thereafter, the addition can be followed by addition of a blocked mercapto group such as thiolacetic acid ($CH_3COSH$) across the maleimido-double bond. After cleavage of the acyl blocking group, a disulfide bond is formed between the deblocked linking group mercaptan and the mercaptan of the cysteine residue of the protein.

Antigenic carriers can be utilized to potentiate or boost the immune response (immunopotentiation), or to direct the type of immune response by use of the inoculum in combination with the carrier. See, for example, the teachings of Milich et al., in U.S. Pat. Nos. 4,599,231, 4,599,230 and 4,683,136, and the teachings of Thornton et al., in U.S. Pat. Nos. 4,818,527 and 4,882,145.

Other means of immunopotentiation include the use of liposomes and immuno-stimulating complex (ISCOM) particles. The unique versatility of liposomes lies in their size adjustability, surface characteristics, lipid composition and ways in which they can accommodate antigens. Methods to form liposomes are known in the art. See, for example, Prescott, Ed., *Methods in Cell Biology*, Vol. XIV, Academic Press, N.Y. (1976) p.33 et seq. In ISCOM particles, the cage-like matrix is composed of Quil A, extracted from the bark of a South American tree. A strong immune response is evoked by antigenic proteins or peptides attached by hydrophobic interaction with the matrix surface.

The choice of carrier is more dependent upon the ultimate use of the immunogen than upon the determinant portion of the immunogen, and is based upon criteria not particularly involved in the present invention. For example, because an inoculum is to be used in a host mammal, a carrier that does not generate an untoward reaction in the particular mammal is selected, as is well-known.

An inoculum is conventionally administered parenterally, by injection, for example, either subcutaneously or intramuscularly. Additional formulations that are suitable for other modes of administration include suppositories and, in some cases, oral formulations. For suppositories, traditional binders and carriers can include, for example, polyalkylene glycols or triglycerides; such suppositories may be formed from mixtures containing the active ingredient in the range of 0.5 percent to 10 percent, preferably 1–2 percent. Oral formulations include such normally employed excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders and contain 10–95 percent of active ingredient, preferably 25–70 percent.

An isolated polypeptide of this invention can be formulated into an inoculum as a neutral or salt form. Pharmaceutically acceptable salts, include the acid addition salts (formed with the free amino groups of the protein or antigen) and which are formed with inorganic acids such as, for example, hydrochloric or phosphoric acids, or such organic acids as acetic, oxalic, tartaric, mandelic, and the like. Salts formed with the free carboxyl groups can also be prepared from inorganic bases such as, for example, sodium, potassium, ammonium, calcium, or ferric hydroxides, and such organic bases as isopropylamine, trimethylamine, histidine, procaine, and the like.

The inoculum is administered in a manner compatible with the dosage formulation, and in such amount as is immunogenic and effective to induce an antibody-producing immune response. The quantity of inoculum to be administered to achieve a desired result depend on the judgement of the practitioner and are peculiar to each individual host mammal, but are well known for laboratory hosts such as mice, rats, rabbits, goats and the like.

An inoculum can also include an adjuvant as part of the excipient, as noted before. Adjuvants such as complete Freund's adjuvant (CFA), incomplete Freund's adjuvant (IFA) for use in laboratory mammals are well known in the art. Pharmaceutically acceptable adjuvants such as alum can also be used. An exemplary inoculum thus comprises one ml of phosphate buffered saline (PBS) containing about 50 to 200 μg of an isolated polypeptide of this invention adsorbed onto about 0.5 mg to about 2.5 mg of alum, or to 0.1 percent to 1 percent $Al(OH)_3$. A preferred inoculum comprises 1 ml of PBS containing 100 μg of the polypeptide adsorbed onto 2.5 mg of alum carrier.

After administration of the inoculum, the host mammal receiving the inoculum is maintained for a time period sufficient for the immune system of the mammal to respond immunologically, typically on the order of 2 to 8 weeks, as is well known, by the production of antibodies immunoreactive with the Pl$^A$-containing immunogen.

The isolated polypeptides, fusion polypeptides and antibodies that immunoreact with the native GPIIIa Pl$^{A1}$ or Pl$^{A2}$ determinants of the present invention can be used in diagnostic methods and systems for typing platelets and for detecting antibodies that immunoreact with the native GPIIIa Pl$^{A1}$ or Pl$^{A2}$ determinants as discussed hereinafter.

G. Diagnostic Methods

A method for detecting antibodies that immunoreact with one but not the other native GPIIIa Pl$^{A1}$ or Pl$^{A2}$ determinants and a method for typing paltelets are also contemplated by the present invention.

The platelet typing method is used to characterize platelets as expressing one or the other of the native GPIIIa Pl$^{A1}$ or Pl$^{A2}$ determinants. That method can be used to screen donor and recipient blood and, thus, identify platelet incompatibility problems before they occur so that conditions such as PTP can be avoided.

In addition, the platelet typing method and the method for detecting antibodies that immunoreact with native GPIIIa Pl$^{A1}$ or Pl$^{A2}$ determinants can be used to test platelets and blood of prospective parents to identify possible problems of platelet incompatibility during prenancy and at birth as in NAIT.

In one embodiment, therefore, the present invention contemplates a method for detecting the presence of specific GPIIIa Pl$^A$ alloantigens. To detect the presence of antibodies that immunoreact with the native GPIIIa Pl$^{A1}$ determinant in a patient, an antibody-containing body sample, and preferably a body fluid sample such as blood, plasma, serum, urine or saliva from the patient, is admixed under biological assay conditions with an antigen that is an isolated polypeptide or fusion polypeptide that expresses the native GPIIIa protein Pl$^{A1}$ or Pl$^{A2}$ determinant, contains about 65 to about 266 amino acid residues of the GPIIIa protein sequence and includes the amino acid residue sequence of SEQ ID NO:1 to form an aqueous immunoreaction admixture. The admixture is maintained under biological assay conditions for a period of time sufficient to permit the formation of an immunoreaction product (immunocomplex) between any of the antibodies and antigen. The presence, and preferably the amount, of complex can then be detected as described herein. The presence of the complex is indicative of antibodies that immunoreact with the native GPIIIa Pl$^{A1}$ or Pl$^{A2}$ determinant.

Preferably, for detection of antibodies to the Pl$^{A1}$ determinant, the antigen used in that method is selected from the group consisting of SEQ ID NO:3, SEQ ID NO:7, SEQ ID NO:11, SEQ ID NO:13, SEQ ID NO:15, SEQ ID NO:17, SEQ ID NO:19, and SEQ ID NO:7 operatively linked to the carboxy-terminus of β-galactosidase. To detect the presence of antibodies that immunoreact with the native GPIIIa Pl$^{A2}$ determinant in the above method, the antigen preferably used is selected from the group consisting of SEQ ID NO:5, SEQ ID NO:9, SEQ ID NO:21, SEQ ID NO:23, SEQ ID NO:25, SEQ ID NO:27, SEQ ID NO:29, and SEQ ID NO:9 operatively linked to the carboxy-terminus of β-galactosidase.

In a preferred embodiment, the presence of the immunoreaction product formed between the isolated polypeptide or fusion polypeptide and a patient's antibodies is detected by using a specific binding reagent as discussed in greater detail hereinafter. A labeled specific binding agent comprises a specific binding agent and a label as described herein.

For example, the immunoreaction product is first admixed with a labeled specific binding agent to form a labeling admixture. The labeling admixture is then maintained under conditions compatible with specific binding and for a time period sufficient for any immunoreaction product present to bind with the labeled specific binding agent and form a labeled product. The presence, and preferably amount, of labeled product formed is then detected to indicate the presence or amount of immunoreaction product.

In a preferred embodiment, the method of the present invention is practiced in a manner whereby the immunocomplex is formed and detected in a solid phase, as disclosed for the systems herein.

Thus, in a preferred diagnostic method, the isolated polypeptide or fusion polypeptide is affixed to a solid matrix to form the solid phase. Methods of affixation to a solid matrix are well known in the art. Such methods include adsorption, which is preferred, use of a second antibody to the complex such as antibodies directed to another portion of GPIIIa included in the polypeptide or antibodies to β-galactosidase where a β-galactosidase or portion thereof is fused to a contemplated polypeptide. Affixation by covalent bond formation is also contemplated. Specific solid matrices are discussed in greater detail hereinafter.

It is further preferred that the specific binding agent is protein A, or an anti-human Ig, such as IgG or IgM, that can complex with the antibodies immunocomplexed in the solid phase with that isolated polypeptide. Most preferred is the use of a labeled specific binding agent where the label is a radioactive isotope, an enzyme, biotin or a fluorescence marker such as lanthanide.

In this solid phase embodiment, it is particularly preferred to use a recombinant fusion polypeptide as described hereinbefore.

In another preferred diagnostic method, the isolated polypeptide or fusion polypeptide of the present invention is affixed to solid matrix as described above, and dilutions of the biological sample are subjected to the immunocomplexing step by contacting dilutions of the sample with the solid support, maintaining that contact under biological assay conditions for a period of time sufficient for a solid phase-bound immunocomplex to form, separating the solid and liquid phases and removing non-bound materials. Due to the multivalence of antibodies present in biological samples, subsequently added labeled polypeptide or fusion polypeptide becomes attached to the solid phase by the sample antibody serving as bridge between the solid phase polypeptide and the soluble, labeled molecules. The presence of label in the solid phase indicates the presence and preferably the amount of specific antibody in the sample. One skilled in the art can determine a range of dilutions and determine therefrom a concentration of labeled antigen in the solid phase.

The biological sample and the isolated polypeptides of the invention can be admixed prior to, or simultaneously with contacting the biological sample with the solid phase allowing the trimolecular complex to form at the solid phase by utilizing the bridging property of bivalent or multivalent specific antibody. As a particularly useful label, biotinylated polypeptides of the invention can be the labeled antigen, permitting the subsequent detection by addition of an enzyme-streptavidin, or an enzyme-avidin complex, followed by the appropriate substrate. Enzymes such as horseradish peroxidase, alkaline phosphatase, β-galactosidase or urease are frequently used and these, and other, along with several appropriate substrates are commercially available. Preferred labels with a marker which allows direct detection of the formed complex include the use of a radioactive isotope, such as, e.g. iodine, or a lanthanide chelate such as europium.

In another embodiment, the present invention complates a method for typing platelets that comprises (a) admixing platelets from a donor in an aqueous medium with antibodies that immunoreact with one or the other but not both of the GPIIIa $Pl^{A1}$ and $Pl^{A2}$ determinants (as discussed before) to form an aqueous immunoreaction admixture;

(b) maintaining the aqueous immunoreaction admixture under biological assay conditions for a time period sufficient for those admixed antibodies to immunoreact and form an immunoreaction product; and (c) detecting the presence of any of said immunoreaction product and thereby the presence of one or the other of the GPIIIa $Pl^{A1}$ or $Pl^{A2}$ determinants and the platelet type.

It is preferred that the antibodies utilized in this assay be from an animal species other than that of the platelet donor. Thus, the antibodies can, for example, be produced from a mouse, rat, rabbit, goat, horse or the like. As such, the presence of an immunoreaction between the admixed antibodies and the platelets can be detected by further immunoreaction with species-specific antibo-antibodies containing a label such as an enzyme or radiactive element as discussed before.

More preferably, the admixed anti-GPIIIa $Pl^{A1}$ or $Pl^{A2}$ determinant antibodies include their own label as discussed herein so that a further immunoreaction is unnecessary. Most preferably, those anti-$Pl^{A}$ antibodies are monocloanl antibodies that include an enzyme label such as alkaline phospotase or horseradish peroxidase.

In a preferred embodiment, the antibodies used in that method immunoreact with the gPIIIa $Pl^{A1}$ determinant and not the GPIIIa $Pl^{A2}$ determinant.

In another preferred embodiment, the antibodies used in that method immunoreact with the GPIIIa $Pl^{A2}$ determinant but not the GPIIIa $Pl^{A1}$ determinant.

Preferably, the antibodies used in both embodiments are monoclonal antibodies.

A method for typing platelets is also contemplated within the invention. As set forth before, various well known heterogeneous and homogeneous protocols can be employed in the platelet typing method. Preferably, a platelet-containing body sample from a donor is admixed in an aqueous composition with anti-$Pl^{A1}$ or $Pl^{A2}$ antibodies to form an immunoreaction admixture.

The immunoreaction admixture formed above is maintained under biological assay conditions for a time period sufficient for the antibodies to immunoreact with their antigens on the platelets. The formation of an immunocomplex indicates the presence of platelets expressing a particular antigen, and that formation can be detected by any means discussed herein.

The maintenance time for an immunoreaction discussed before to take place can vary widely, as is well known. Maintenance times typically range from about one minute to about two hours, with times of about 30 to about 90 minutes being typically utilized.

An antibody molecule includes intact antibodies, or the binding site-containing (paratope-containing) portions thereof. Exemplary paratope-containing portions include Fab, F(ab')$_2$ and F$_V$ portions as are well known. In addition, where an antibody Fc portion is present, that portion can have the amino acid residue sequence characteristic of an animal different from the paratope-containing portion. For example, a human Fc portion can be present along with a mouse binding site-containing portion as can be accomplished by genetic engineering techniques as are well known.

The "biological assay conditions" employed in the present assay methods are selected to maintain the biological activities of the sample being assayed, as well as the antibodies and polypeptides used in the assay. Typically acceptable "biological assay conditions" include a temperature in the range of about 4° C. through about 45° C., preferably about 37° C.; a pH value in the range of about 5 through about 9, preferably about 7; and an ionic strength ranging from that for distilled water to that of about 1M sodium chloride, preferably about that of physiological saline. Methods for optimizing such conditions are known to the skilled practitioner.

The manner of determining the presence or amount of an immunocomplex formed in a subject assay depends upon the method desired to identify the immunocomplex. For instance, an antibody used in the assay can be labeled prior to or subsequent to forming an immunocomplex with the platelets. The labeled immunocomplex can be quantitated by methods appropriate for detecting the respective label, e.g., radiation detection when a radioactive label is used, fluorescence detection when a fluorescent is employed, reaction with avidin when a biotin label is employed, conversion of an enzyme substrate into a detectible product when an enzyme label is used, and the like. Alternatively, an unlabeled immunocomplex can be detected by forming an immunoreaction product between the immunocomplex and a labeled substance that specifically binds the immunocomplex, e.g., a labeled anti-antibody. A label is thereby attached to the assayed immunocomplex, which affords ready detection.

H. Diagnostic Systems

A diagnostic system in kit form includes, in an amount sufficient for at least one assay according to the methods described herein, an isolated polypeptide or fusion polypeptide of the present invention, or an antibodies of this invention that immunoreact with the native GPIIIa $Pl^{A1}$ or $Pl^{A2}$ determinants, as a separately packaged reagent. Instructions for use of the packaged reagent are also typically included.

"Instructions for use" typically include a tangible expression describing the reagent concentration or at least one assay method parameter such as the relative amounts of reagent arnd sample to be admixed, maintenance time periods for reagent/sample admixtures, temperature, buffer conditions and the like.

In preferred embodiments, a diagnostic system of the present invention further includes a label or indicating means capable of signaling the formation of a immunoreaction product prepared in an above method.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in a reagent species such as antibodies, a polypeptide or fusion polypeptide, or can be used separately, and those atoms or molecules can be used in conjunction with additional reagents. Such labels are themselves well-known in clinical diagnostic chemistry and constitute a part of this invention only insofar as they are utilized with otherwise novel proteins, methods and/or systems.

The label can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanite (FITC), 5-dimethylamine-1- naphthalenesulfonyl chloride (DANSC), tetramethylrhodamine isothiocyanate (TRITC), lissamine, rhodamine 8200 sulphonyl chloride (RB 200 SC), a chelate-lanthanide bound (e.g., Eu, Tb, Sm) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189–231 (1982), which is incorporated herein by reference.

In preferred embodiments, the label is an enzyme, such as horseradish peroxidase (HRP) used illustratively herein, glucose oxidase, alkaline phosphatase or the like. In such cases where the principal label is an enzyme such as HRP or glucose oxidase, additional reagents are required to visualize the fact that an antibody-antigen complex (immunoreactant) has formed. Such additional reagents for HRP include hydrogen peroxide and an oxidation dye precursor such as diaminobenzidine. An additional reagent useful with HRP is 2,2'-azinobis(3-ethylbenzothiazoline-6-sulfonic acid) (ABTS).

Radioactive elements are also useful as labeling agents. An exemplary radiolabeling agent is a radioactive element that produces gamma ray emissions. Elements which themselves emit gamma rays, such as $^{124}I$, $^{125}I$, $^{128}I$, $^{131}I$ and 51Cr represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such as $^{111}$ indium, $^3H$, $^{35}S$, $^{14}C$, or $^{32}P$.

Additional labels have been described in the art and are suitable for use in the diagnostic systems of this invention. For example, the specific affinity found between pairs of molecules can be used, one as a label affixed to the specific binding agent and the other as a means to detect the presence of the label. Exemplary pairs are biotin:avidin, where biotin is the label, and peroxidase:anti-peroxidase (PAP), where peroxidase is the label.

The linking of labels; i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity that selectively binds a reagent species, which in turn reacts with a product of the present invention but is not itself a protein expression product of the present invention. Exemplary specific binding agents are antibody molecules such as anti-human IgG or anti-human IgM, complement proteins or fragments thereof, protein A, and the like. Preferably the specific binding agent can bind the antibodies that immunoreact with the native GPIIIa $Pl^{A1}$ or $Pl^{A2}$ determinants when those antibodies are present as part of an immunoreaction product or immunocomplex.

In a preferred embodiment, the specific binding agent is labeled. However, where the diagnostic system includes a specific binding agent that is not labeled, the agent is typically used as an amplifying means or reagent. In these embodiments, the labeled specific binding agent specifically binds the amplifying means when the amplifying means is bound to a reagent spacies-containing complex.

A diagnostic kit of the present invention can be used, for example, in a previously described method in an "ELISA" format to detect the presence or quantity of antibodies in a body fluid sample such as serum, plasma or saliva. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; No. 3,850,752; and No. 4,016,043, which are all incorporated herein by reference.

Thus, in a preferred embodiment, a before-discussed, contemplated isolated polypeptide, fusion polypeptide or antibodies that immunoreact with the native GPIIIa $Pl^{A1}$ or $Pl^{A2}$ determinants of the present invention can be affixed to a solid matrix to form a solid support that is separately packaged in a subject diagnostic system.

Useful solid matrices are well known in the art. Such materials include the cross-linked dextran available under the trademark SEPHADEX from Pharmacia Fine Chemicals (Piscataway, N.J.); agarose; beads of polystyrene about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microliter plate such as those made from polystyrene or polyvinylchloride.

The following examples illustrate particular embodiments of the invention and are not limiting of the specification and claims in any way.

I. Results

A platelet GPIIIa epitope library was constructed by insertion of randomly cleaved GPIIIa cDNA fragments in the prokaryotic expression vector λgt22. This library expresses random fragments, averaging about 100–200 amino acid residues in length, of GPIIIa fused into β-galactosidase.

The μgt22-GPIIIa epitope library was screened with purified anti-$Pl^{A1}$ antibodies for clones expressing the $Pl^{A1}$ epitope. Five independent clones that reacted with purified anti-$Pl^{A1}$ antibodies from patient number 1 were isolated, and sequence analysis of the DNA from each of the recombinant phage localized the $Pl^{A1}$ epitope to the amino-terminal end of GPIIIa (FIG. 1).

Fragments from throughout the GPIIIa sequence were isolated by screening the λgt22-GPIIIa epitope library with polyclonal anti-GPIIIa antibodies. These other regions of GPIIIa, however, failed to react with the anti-$Pl^{A1}$ antibodies from four patients.

The smallest fragment containing the $Pl^{A1}$ antigen expressed the amino-terminal 65 residues of mature GPIIIa and the 27 residue signal sequence (FIG. 2). All the clones obtained overlapped this region and reacted with purified anti-$Pl^{A1}$ antibodies from four individuals indicating that the $Pl^{A1}$ epitope was located within the amino-terminal 65 residues of GPIIIa.

Residue 33 of mature GPIIIa is responsible for the two $Pl^A$ phenotypes [Newman et al., *J. Clin. Invest.*, 83:1778 (1989); Goldberger et al., *Blood*, 78:681 (1991)]. The $Pl^{A2}$ (proline 33) phenotype was constructed in the λgt22 clone expressing the amino-terminal 65 residues of GPIIIa by a T→$C_{196}$ substitution.

The replacement of leucine[33] with a proline resulted in loss of anti-Pl$^{A1}$ antibody reactivity, however, reactivity with the polyclonal anti-GPIIIa antibodies remained intact as evidenced by immunoreaction with phage plaques. Therefore, residue 33 was important in formation of the Pl$^{A1}$ epitope in this 7 kDa amino terminal fragment of GPIIIa.

J. Methods and Materials

EXAMPLE 1

Anti-Pl$^{A1}$ alloantibodies

Anti-Pl$^{A1}$ alloantibody from the plasma of four patients with PTP [plasma kindly provided by Dr. S. Schinke, San Jacinto (patient 1), Dr. G. Schmidt, City of Hope Medical Center, Duarte (patient 2), and Dr. V. Blanchette, Hospital for Sick Children, Toronto (patients 3 and 4)] was affinity-purified using the platelet glycoprotein complex GPIIb-IIIa coupled to CnBr-sepharose-4BCL (Pharmacia, Piscataway, N.J.).

Washed normal platelets were solubilized in isotonic citrate buffer, pH 6.5, containing 1 percent Triton X-100 for 30 minutes at 4° C. followed by centrifugation at 100,000×g for 60 minutes at 4° C. The supernatant was incubated overnight at 4° C. with murine monoclonal anti-GPIIb (2A9, provided by Dr. V. Woods, University of California at San Diego) coupled to CnBr-sepharose-4BCL. After washing with PBS, the bound GPIIb-IIIa was eluted with 0.1M diethylamine in 1 percent octaglucopyranoside (OPG) in PBS, pH 10, and immediately dialysed against 0.1M phosphate buffer containing 1 percent OPG. The purified GPIIb-IIIa was then coupled to CnBr-sepharose-4BCL. The GPIIb-IIIa-sepharose was incubated overnight at 4° C. with plasma, washed, bound alloantibody eluted with 0.1M glycine, pH 2.5, immediately neutralized with 1M Tris, pH 9, and dialysed in PBS. The antibody eluate was titered by an antigen capture assay [Woods et al., *Blood*, 63:368 (1984)].

EXAMPLE 2

Epitope Library Construction and Screening

A 2.6 kb double stranded fragment encoding full length GPIIIa was isolated by cleavage of the plasmid BS3a [O'Toole et al., *Blood*, 74:14 (1989)] with the restriction enzymes Sph I and Spe I, and subsequent purification of the 2.6 kb band from an agarose gel. Five ug of the isolated band was then digested in 0.5 ml of 20 mM Tris-Cl pH7.5 and 1.5 mM MnCl$_2$ with 0.5 ng DNase I for 30 minutes at 37° C. The reaction was immediately stopped by phenol:chloroform extraction of the reaction mixture.

After ethanol precipitation of the resulting GPIIIa DNA, the fragments were polished with T4 DNA polymerase, ligated with the double stranded Sal I linker GGTCGACC (only the sense sequence being shown; SEQ ID NO:30), cleaved with the restriction enzyme Sal I, and ligated into dephosphorylated Sal I digested λgt22 (Promega Corp., Madison, Wis.). The ligated DNA was then packaged and the unamplified library titered on *E. coli* Y1090 and found to contain 2×10$^4$ total phage (84 percent recombinant).

EXAMPLE 3

Screening of λgt22 recombinant phage

Five thousand plaques/plate of the recombinant λgt22-GPIIIa epitope library were plated on *E. coli* Y1090. The lacZ gene was induced with isopropyl-β-D-thiogalactoside (IPTG) saturated filters as described [Young et al., *Proc. Nat.*

*Acad. Sci., USA*, 80:1194 (1983)]. The filters were then screened with either polyclonal rabbit anti-GPIIIa antibodies (1:250 dilution) [Loftus et al., *Science*, 249:915 (1990)] pre-absorbed with a lysate of λgt22 infected *E. coli*, Y1090, pre-absorbed normal rabbit serum (1:250 dilution), or purified anti-Pl$^{A1}$ antibodies (1:100 dilution).

Bound antibodies were detected by reaction with a peroxidase conjugated anti-rabbit immunoglobulin G (IgG) or anti-human IgG secondary antibody and developed with the chromogenic substrate o-phenylenediamine. The purified anti-GPIIIa and anti-Pl$^{A1}$ positive phage were screened by plating 1 to 2 hundred plaques of a 1:1 mixture of λt22 and a recombinant λgt22 construct on *E. coli*, Y1090. The lacZ gene was induced, the filters were cut into pieces, and screened with pre-absorbed anti-GPIIIa antibodies, normal rabbit serum, anti-Pl$^{A1}$ antibodies, and normal human serum.

EXAMPLE 4

Sequencing of GPIIIa Inserts

Recombinant λgt22 DNA was isolated as described [*Molecular Cloning: A Laboratory Manual*, ed. 2, Sambrook et al., eds., Cold Spring Harbor Laboratory Press (1989)], cut with the restriction enzymes Eco RI and Not I, and subcloned by standard techniques into the plasmid Bluescript II SK +/−(Stratagene, La Jolla, Calif.). Both strands were then sequenced using the T7 and T3 primers (Stratagene) by the dideoxy sequencing method [Sanger et al., *Proc. Natl. Acad. Sci., USA*, 74:5463 (1977) to determine the boundaries of the DNA fragments. The plasmid subclone of the smallest anti-Pl$^{A1}$ positive GPIIIa fragment (292 bp) was completely sequenced and subsequently used for mutagenesis.

EXAMPLE 5

In Vitro mutagenesis

Oligonucleotide directed mutagenesis was performed using a combination of the primer extension method [Zollar et al., *Nuc. Acids. Res.*, 10:6487 (1982)] and the strand selection method [Kunkel et al., *Proc. Natl. Acad. Sci. USA*, 82:488 (1985)] which provides strong biological selection against the non-mutagenized strand. The single T→C substitution at base 196 of GPIIIa was introduced into the 292 bp fragment using the oligonucleotide GGTGAGCCCG-GAGGCAGGGCCTCA (SEQ ID NO:31).

Inserts with the expected mutation were screened for the appearance of an Nci I site [Newman et al., *J. Clin Invest.*, 83:1778 (1989)] and then completely sequenced. The insert with the T→C substitution was then subcloned back into λgt22 to form the Pl$^{A2}$ epitope-containing fusion polypeptide.

EXAMPLE 6

Preparation and Isolation of Fn Fragment-MBP Fusion Proteins

Two MBP-encoding plasmids, PMAL p2 and PMAL c2, are used as vectors for expressing an instant fusion protein in *E. coli*. The MBP region of the fused protein permits ready purification of the fused product from other cellular proteins. These vectors are constructed by well known techniques [*Molecular Cloning: A Laboratory Manual*, 2 ed., Sambrook, et al. eds, Cold Spring Harbor Laboratory Press, Cold Spring Harbor, N.Y. (1989)] following the procedures desribed hereinbelow. A lengthy discussion of predecessors to these vectors; i.e., vectors pPR734 and pIH821, including restriction maps, constituent genes and encoded sequences, uses and protocols for use can be found in *Current Protocols in Molecular Biology*, Ausubel et al., eds., Greene Publishing Associates and Wiley-Interscience, New York (1989) pages 16.6.1–16.6.12.

A. Construction of MBP Vector

The preparation of an exemplary MBP-expression vector is as follows, using a cDNA clone containing the $PI^{A1}$-encoding DNA of SEQ ID NO:2 that encodes the 65-amino acid residue epitope for $PI^{A1}$ contained in the Eco RI-Not I fragment discussed before. This fragment contains not only the DNA that encodes the desired $PI^{A1}$ epitope, but also contains DNA from the λgt22 polylinker region, with the Eco RI site being at the 5' end and the Not I site at the 3' end, and Sal I and Xba I sites therebetween. It is also to be understood that another of the cDNA's encoding the $PI^{A1}$ or $PI^{A2}$ epitopes discussed herein can also be used similarly.

Thus, the before-described λgt22 vector containing the 292 bp fragment encoding the anti-$PI^{A1}$ positive GPIIIa fragment is digested with Sal I. The maltose binding protein fusion protein vector PMAL c2 (New England Biolabs, Inc., Beverly, Mass.) is digested with Sal I to produce Sal I cohesive termini. The $PI^{A1}$ encoding Sal I—Sal I fragment is ligated into the vector using DNA T4 ligase to form a fusion polypeptide-forming construct having the cloned $PI^{A1}$-coding gene fragment operatively ligated to the MBP-coding gene fragment. The resulting recombinant DNA molecule can express a MBP-$PI^{A1}$ fusion polypeptide.

As a result of the above maniupulations, the carboxy-terminus of the expressed fusion polypeptide includes a sequence of several non-GPIIIa residues. In addition, as discussed in detail hereinafter, the Sal I site of the pMAL™c2 vector is located near the 3' end of the polylinker region. Thus, even after cleavage with factor Xa, the resulting recombinant polypeptide includes several vector-induced residues at the amino-terminus of the molecules. These vector-induced residues are in addition to those induced by the previously-discussed addition of the Sal I linkers.

It should be understood by those skilled in the art that additional well-known manipulations can be utilized to shorten the expressed fusion polypeptide to eliminate vector-induced residues. One such manipulation utilizes an inframe 5'-blunt ended $PI^A$ epitope-encoding DNA fragment that is inserted into the Xmn I site of a PMAL c2 or PML p2 vector so that after cleavage with factor Xa, no vector-induced amino acid residues are present in the recombinant polypeptide. Another manipulation utilzies an inframe stop codon ligated to the 3' end of the GPIIIa coding sequence, that codon itself being ligated to a restriction site further downstream that can be utilized to insert the DNA. This manipulation removes vector-induced residues from the carboxy-terminus of the recombinant polypeptide.

Vectors PMAL c2 and PMAL p2 are obtained from New England Biolabs (Beverly, Mass.). The vectors each have a malE linked via a poiylinker to a lac Z gene. Vector PMAL c2 is identical to vector PMAL p2 except that vector PMAL c2 has a deletion of the malE signal (leader) sequence 2–26, which, when present, facilitates export of fusion protein to the periplasm. The vectors each have a tac promoter (Ptac) upstream of the malE gene. A lac $I^Q$ suppressor gene immediately upstream of the tac promoter permits suppression of expression activity until IPTG (isopropyl β-D-thiogalactoside) is used to induce expression. The remaining vector backbone is from Ava1 (filled in) to Eco R1 (filled in) of pKK233-2 (Pharmacia, Piscataway, N.J.).

The important components of the maltose-binding protein fusion expression system (MBP expression system) are the promoter (PtacII) previously described by Amann et al., *Gene*, 25:167–178 (1983); the maltose binding protein-lacZα and fusion gene (malE-LacZα) previously described by Guan et al., *Gene*, 67:21–30 (1987); the rrn B ribosomal transcription terminator previously described by Brosius et al., *Proc. Natl. Acad. Sci. USA*, 81:6929–6933 (1984) and commercially available in the PMAL c2 (pIH821) and PMAL p2 (pPR734) vectors (New England Biolabs, Beverly, Mass.) and in the pKK223-3 and pKK233-2 (Pharmacia, Piscataway, N.J.).

The MBP expression system optionally contains the gene coding for the lac repressor gene (lac I) previously described by Farabaugh, *Nature*, 274:765–769 (1978). If the lac I gene is not present on the expression vector it can be provided in trans by using the bacterial strains expressing the lambda repressor such as JM101, JM105, JM107, JM109 (ATCC #33323) and JM110 (ATCC #47013) described by Yanisch-Perron et al., *Gene*, 33:103 (1985) which are commercially available from Stratagene (La Jolla, Calif.).

The individual nucleic acid segments containing the components of this expression system are operatively ligated together (ligated) using standard molecular biology techniques, such as those described in *Molecular Cloning: A Laboratory Manual*. 2nd ed., Sambrook et al., eds, Cold Spring Harbor Laboratories, N.Y. (1989). When necessary, the reading frame of the various components is adjusted using synthetic linkers, various fill-in reactions or various exonucleoses. In addition, various deletions and adjustments in the reading frame are easily made using loop-out mutagenesis and the commercially available mutagenesis kits such as the mutagene kit from Bio Rad Laboratories (Richmond, Calif.).

Each of the required components of the expression system will now be described in detail. The Ptac II promoter previously described by Amann et al., Gene, 25:167–178 (1983) can be isolated from a number of available vectors, such as PKK 223-3 (Pharmacia), PIH821 and pPR734 (New England BicLabs, Beverly, Mass.), Ptac II (ATCC #37245) and Ptac 12 (ATCC #37138) described by Amann et al., *Gene*, 25:167–178 (1983). For example, the Ptac II promoter can be isolated using restriction endonucleases from Ptac II using Eco RI and Hind III or Cla I and Hind III.

The maltose binding protein-lacZα fusion gene (malE-lacZα) previously described by Guan et al., *Gene*, 67:21–30 (1987) contains the malE gene on a Hinf I restriction endonuclease fragment isolated from the chromosome of an *E. coli*, such as HB101 (ATCC #33694) or wild type *E. coli*, K12. The malE gene has been sequenced by Duplay et al., *J. Biol. Chem.*, 259:10606–10613 (1984) and therefore probes specific for the malE gene can be easily synthesized permitting the malE gene to be isolated from *E. coli*, using standard cloning protocols. Alternatively, the malE gene can be chemically synthesized in segments and these segments joined using T4 DNA Ligase to produce the malE gene. The mature maltose binding protein (the malE gene product) is coded for by codons 28–342 of the malE gene sequence as described by Duplay et al., *J. Biol. Chem.*, 259:10606–10613 (1984). The expression vector can either contain the entire malE gene coding for the maltose binding protein leader sequence and codons coding for the mature maltose binding protein, eg. as in PMAL™p2, or only the portion of the malE gene coding for the mature maltose binding protein, e.g. as in PMAL c2.

The remainder of the maltose binding protein-lacZα fusion gene contains the portion of the lacZ gene coding for the shorter alpha (α) peptide of the lac gene (approximately 107 amino acids in length). This laczα gene can be isolated from plasmid vector pUC 19 described by Yanisch-Perron et al., *Gene*, 33:103–119 (1985) and is commercially available. The laczα gene and the malE gene are linked together using a polylinker that contains useful restriction endonuclease recognition sequences, and cloning into which permits blue-to-white screening for inserts.

The rrn B ribosomal transcription terminator was previously described by Brosius et al., *Proc. Natl. Acad. Sci. USA*, 81:6929 (1984) and Brosius et al., *Plasmid*, 6:112–118 (1981). The rrn B ribosomal transcription terminators can be easily isolated from available vectors, such as PEA300 (ATCC #37181), PKK 223-3 and PKK 233-2 (Pharmacia), and PIH821 and PPR734 (New England Biolabs). For example, the rrn B ribosomal transcription terminator can be isolated from pKK223-3 using Hind III and Pvu I restriction endonucleases.

The lacI gene coding for the lambda repressor protein has been sequenced by Farabaugh, *Nature*, 274:765 (1978). In addition, the lacI gene is in several available vectors, such as pBluescript II KS and pBluescript SK (Stratagene); and pUC 18 and pUC 19 (Pharmacia). The lacI gene can be isolated from these vectors using restriction endonucleases and standard molecular biology techniques. The lacI gene can be present in the expression vector or present in the bacteria the expression vector is grown in.

The multiple cloning site (polylinker) present in the expression vector between the malE and lacZ genes is shown in Table 1 and listed in the Sequence Listing as SEQ ID NO:32.

TABLE 1

Sequence of Polylinker in Expression System

```
              Xmn I          Eco RI
malE ... ATC GAG GGA AGG ATT TCA GAA TTC Bam HI   Xba I  Sal I   Pst I
     GGA TCC  TCT AGA GTC GAC CTG CAG
         Hind III
     GCA  AGC TTG ... lacZα
```

Restriction endonuclease cleavage sites are shown in the above table above the DNA sequence, and each site is underlined. A four-residue recognition site for factor Xa cleavage of the fusion protein is encoded by the first four codons shown in the table. DNA coding for ten asparagine residues separates the malE gene and the above polylinker.

The multiple cloning site (polylinker) contains a nucleic acid segment that codes for a factor Xa cleavage site located between the malE and lacZ genes, as noted above. A maltose binding protein fusion protein produced by this vector can be cleaved at the factor Xa cleavage site, thereby facilitating the purification of the desired protein and the production of recombinates of ultimately lower molecular weight.

A foreign gene such as that encoding $PI^{A1}$ or $PI^{A2}$ as described herein can be inserted into one or more restriction sites illustated in Table 1. When the Xmn I site is used, and the expressed fusion protein cleaved with factor Xa, no length is added to the $PI^{A1}$ or $PI^{A2}$ polypeptide because of the vector. When another site is used, up to about 15 vector-derived residues can be added, depending upon which site is used.

Once the plasmid vector containing a contemplated $PI^{A1}$ or $PI^{A2}$ DNA insert is prepared as desscribed above, the vector is used to transform *E. coli* following standard techniques. Any transformable *E. coli*, can be used, with strains PR722 or ER1451 (available from New England Biolabs) being particularly suitable. The resulting transformed *E. coli*, are then grown in culture.

B. Expression of MBP Fusion Protein

A small scale study is described to determine the behavior of a particular MBP fusion protein. This protocol results in three crude extract fractions; a total cell crude extract, a suspension of the insoluble material from the crude extract, and a periplasmic fraction prepared by the cold osmotic shock procedure.

Inoculate 80 ml rich broth+glucose and ampicillin (per liter, 10 g Tryptone, 5 g yeast extract, 5 g NaCl, 1 g glucose, autoclave, add ampicillin to 100 μg/l) with transformed *E. coli*, cells containing the fusion plasmid produced above. Grow at 37° C. with good aeration to $2 \times 10^8$ cells/ml. Take a sample of 1 ml and centrifuge for two minutes in a microfuge (uninduced cells). Discard supernatant and resuspend the cells in 100 μl SDS-PAGE sample buffer. Vortex and place on ice.

Add IPTG (isopropylthiogalactoside) to the remaining culture to give a final concentration of 0.3 mM, e.g., 0.24 ml of a 0.1M stock in $H_2O$. Continue incubation at 37° C. for 2 hours. Take a 1 ml sample and centrifuge for 2 minutes in a microfuge (induce cells). Discard supernatant and resuspend the cells in 150 μl SDS-PAGE sample buffer. Vortex to resuspend cells and place on ice.

Divide the culture into two aliquots and harvest the cells by centrifugation at 4000×g for 10 minutes. Discard the supernatant and resuspend one pellet (Sample A) in 5 ml 10 mM sodium phosphate, 30 mM NaCl, 0.25 percent TWEEN 20 (POLYSORBATE 20), 10 mM EDTA, 10 mM EGTA (Sigma E 4378), pH 7.0. Resuspend the other pellet (Sample B) in 10 ml 30 mM Tris-HCl, 20 percent sucrose, pH 8.0 (9 ml for each 0.1 g cells wet weight).

Freeze Sample A in a dry ice-ethanol bath (or about 18 hours at 20° C.) then thaw in cold water. Sonicate the sample and monitor cell breakage by measuring the release of protein using the Bradford assay or absorbance at 280 nm ($A_{280}$), until it reaches a maximum. Centrifuge at 9,000×g for 20 minutes. Decant the supernatant (crude extract 1) and save on ice. Resuspend the pellet in 5 ml 10 mM sodium phosphate, 0.25 percent TWEEN 20(POLYSORBATE 20), 30 mM NaCl, 10 mM EDTA, 10 mM EGTA, pH 7.0. This is a suspension of the insoluble matter (crude extract 2).

Add EDTA to 1 mM of Sample B and incubate for 5–10 minutes at room temperature with shaking or stirring. Centrifuge at 4° C., remove all the supernatant, and resuspend the pellet in 10 ml ice-cold 5 mM $MgSO_4$. Shake or stir for 10 minutes in an ice bath. Centrifuge at 4° C. The supernatant is the cold osmotic shock fluid.

Add 5 μl 2× SDS-PAGE sample buffer to 5 μl of crude extracts 1 and 2 and 10 μl 2× SDS-PAGE sample buffer to 10 μl of the cold osmotic shock fluid. Boil these samples, along with the uninduced and induced cell samples, for 5 minutes. Centrifuge in a microfuge for 2 minutes. Load 20 μl of the uninduced and induced cells samples, and all of the extract samples, on a 10 percent SDS-PAGE gel. An identical SDS-PAGE gel(s) using 1:5 dilutions of the above samples can also be used. A Western blot is then carried out and developed with anti-MBP serum or serum immunospecific for the cloned GPIIIa portion to identify the extract containing the desired epitope.

C. Purification of MBP-Fusion Protein (1) Preparation of Cross-linked Amylose Resin For 300 ml resin, place 10 g. amylose (Sigma, Catalog No. A-7043), 40 ml $H_2O$ and a stirring bar in a 1000 ml beaker and warm to 50° C. with stirring. In a fume hood, add 60 ml 5N NaOH, then 30 ml epichlorhydrin (Sigma, Catalog No. E-4255) with rapid stirring. The suspension will heat up upon gelling. Continue stirring until the suspension forms a solid gel and turns slightly yellow, about 10 minutes. Let cool to room temperature (about 45 minutes—1 hour) then cut the gel into pieces and wash three times with 1000 ml H$_2$O. Transfer the gel to a WARING blender and fragment the gel for about 3–5 seconds. Wash with 1000 ml 50 mM glycine-HCl, 0.5M NaCl, pH 2.0, two times and discharge the fines between washes.

Wash with water three times (keep discharging fines), then with 10 mM sodium phosphate, pH 7.0, three times. Suspend the gel in 10 mM sodium phosphate, 0.02 percent sodium azide, pH 7.0 and store at 4° C. Block non-specific sites on the resin by washing in 1000 ml 3 percent non-fat dry milk overnight at 4° C.

(2) Affinity Chromatoaraphy

The following are protocols for large scale purification of a MBP-fusion protein.

Inoculate 1 liter rich broth, glucose and ampicillin (per liter, 10 g Tryptone, 5 g yeast extract, 5 g NaCl, 1 g glucose, autoclave, add ampicillin to 100 μg/ml) with transformed *E. coli*, cells containing a plasmid that expresses the desired MBP fusion protein. Grow to 2×10$^8$ cells/ml (A$_{600}$ of 0.4). Add IPTG to a final concentration of 0.3 mM, e.g. 85 mg or 3 ml of a 0.1M stock in H$_2$O. Incubate the transformed *E. coli* cells at 37° C. for a time sufficient for expression to take place, such as 1–3 hours.

Harvest the cells by centrifugation at 4000×g and resuspend in 50 ml 10 mM sodium phosphate, 30 mM NaCl, 0.2 percent TWEEN 20 (POLYSORBATE 20), 10 mM EDTA, 10 mM EDTA, 10 mM EGTA (Sigma, Catalog Number E 4378), pH 7.0. Freeze the resuspended sample in a dry ice-ethanol bath (or about 18 hours at 20° C.) and thaw in cold water. Sonicate and monitor cell breakage, by measuring the release of protein using the Bradford assay or A280, until it reaches a maximum. Centrifuge at 9,000×g for 30 minutes and collect the supernate to form a crude extract.

Pour the cross-linked amylose resin into an Erlenmeyer flask and let it settle. Wash the resin in at least an equal volume of column buffer+0.25 percent TWEEN 20 (POLYSORBATE 20) a few times; column buffer=10 mM sodium phosphate, 0.5M NaCl, pH 7.0. Pour a column of about 40–200 ml resin for each liter of culture and wash the column with 3 column volumes the same buffer.

Dilute the crude extract 1:5 with column buffer+0.25 percent TWEEN 20 (POLYSORBATE 20). Load the diluted crude extract at a flow rate of [10×(diameter of column in cm)$^2$]ml/hr. This is about 1 ml/min for a 2.5 cm column. The dilution of the crude extract is aimed at reducing the protein concentration to about 2.5 mg/ml. A good rule of thumb is that 1 g wet weight of cells gives about 120 mg protein.

The crude extract can be passed through the column twice to be sure that all the MBP-fusion polypeptide is bound to the column, but in most cases all the MBP-fusion polypeptide that is competent to bind does so on the first pass. Fusion polypeptide can also be loaded on the resin batch-wise, by incubating crude extract and resin at 4° C. for 2–76 hours with gentle agitation. Wash with 3 column volumes column buffer+0.25 percent TWEEN 20 (POLYSORBATE 20) then wash with 5 column volumes column buffer without TWEEN 20 (POLYSORBATE 20).

Elute the fusion polypeptide with 10 mM sodium phosphate, 0.5M NaCl, 10 mM maltose, pH 7.0. Collect 10–20 fractions each =to ⅕$^{th}$ to ¹⁄₁₀$^{th}$ the column volume and assay the fractions for protein, e.g., by the Bradford assay or A$_{280}$; the fractions containing the MBP-fusion polypeptide have easily detectable protein. The MBP-fused PI$^{A1}$ or PI$^{A2}$ polypeptide elutes directly after the void volume of the column. Pool the protein-containing fractions. Dialyze vs. 4×100 volumes 10 mM Tris-Cl, 100 mM NaCl, pH 8.0 to remove maltose. Concentrate in an AMICON CENCTRI-CON Or CENTRIPREP concentrator, an Amicon stirred-cell concentrator, or the equivalent.

Where the MBP domain is cleaved from the PI$^{A1}$ or PI$^{A2}$ polypeptide by cleavage with factor Xa, further amylose affinity chromatography removes the MBP. The desired PI$^{A1}$ or PI$^{A2}$ polypeptide can thereafter be purified by standard means such as DEAE-sepharose or Mono-Q HPLC chromatography.

Although the present invention has been described in some detail by way of illustration and example for purposes of clarity and understanding, certain obvious modifications can be practiced within the scope of the appended claims.

We claim:

1. An isolated recombinant polypeptide that has about 65 to about 139 amino acid residues from position 1 through about position 139 of the human platelet GPIIIa sequence including the amino acid residue sequence of SEQ ID NO:1, said polypeptide being selected from the group consisting of SEQ ID NO's: 11, 13, 15, 17, 19 and 21, and said polypeptide immunoreacting with antibodies to $Pl^{A1}$ or $Pl^{A2}$ but not with both antibodies and being free from glycosylation.

2. An isolated recombinant fusion polypeptide that comprises a first polypeptide operatively linked to a second polypeptide from two distinct proteins;

said first polypeptide defining the amino acid residue sequence of a polypeptide or protein peptide-bonded to said second polypeptide, said polypeptide or protein not interfering with the immunological binding properties of said second polypeptide; and said second polypeptide having about 65 to about 139 amino acid residues from position 1 through about position 139 of the human platelet GPIIIa sequence, including the amino acid residue sequence of SEQ ID NO:1, said polypeptide being selected from the group consisting of SEQ ID NO's: 11, 13, 15, 17, 19 and 21, and said polypeptide immunoreacting with antibodies to $Pl^{A1}$ or $Pl^{A2}$ but not with both antibodies and being free from glycosylation.

3. The fusion polypeptide according to claim 2 wherein said first polypeptide has the amino acid sequence of β-galactosidase.

* * * * *

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 65 amino acids
      (B) TYPE: amino acid
      (D) TOPOLOGY: linear (ii) MOLECULE TYPE: peptide (ix) FEATURE:
      (A) NAME/KEY: Modified-site
      (B) LOCATION: 33
      (D) OTHER INFORMATION: /label= Xaa
         /note= "Xaa is Leu or Pro."

(xi) SEQUENCE DESCRIPTION: SEQ ID NO:1:

Gly Pro Asn Ile Cys Thr Thr Arg Gly Val Ser Ser Cys Gln Gln Cys
1           5               10              15

```
Leu Ala Val Ser Pro Met Cys Ala Trp Cys Ser Asp Glu Ala Leu Pro
            20                  25                  30

Xaa Gly Ser Pro Arg Cys Asp Leu Lys Glu Asn Leu Leu Lys Asp Asn
            35                  40                  45

Cys Ala Pro Glu Ser Ile Glu Phe Pro Val Ser Glu Ala Arg Val Leu
            50                  55                  60

Glu
65

(2) INFORMATION FOR SEQ ID NO:2:

(i) SEQUENCE CHARACTERISTICS:
        (A) LENGTH: 798 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..798

(xi) SEQUENCE DESCRIPTION: SEQ ID NO:2:

ATG CGA GCG CGG CCG CGG CCC CGG CCG CTC TGG GTG ACT GTG CTG GCG      48
Met Arg Ala Arg Pro Arg Pro Arg Pro Leu Trp Val Thr Val Leu Ala
 1               5                  10                  15

CTG GGG GCG CTG GCG GGC GTT GGC GTA GGA GGG CCC AAC ATC TGT ACC      96
Leu Gly Ala Leu Ala Gly Val Gly Val Gly Gly Pro Asn Ile Cys Thr
            20                  25                  30

ACG CGA GGT GTG AGC TCC TGC CAG CAG TGC CTG GCT GTG AGC CCC ATG     144
Thr Arg Gly Val Ser Ser Cys Gln Gln Cys Leu Ala Val Ser Pro Met
            35                  40                  45

TGT GCC TGG TGC TCT GAT GAG GCC CTG CCT CTG GGC TCA CCT CGC TGT     192
Cys Ala Trp Cys Ser Asp Glu Ala Leu Pro Leu Gly Ser Pro Arg Cys
            50                  55                  60

GAC CTG AAG GAG AAT CTG CTG AAG GAT AAC TGT GCC CCA GAA TCC ATC     240
Asp Leu Lys Glu Asn Leu Leu Lys Asp Asn Cys Ala Pro Glu Ser Ile
 65                  70                  75                  80

GAG TTC CCA GTG AGT GAG GCC CGA GTA CTA GAG GAC AGG CCC CTC AGC     288
Glu Phe Pro Val Ser Glu Ala Arg Val Leu Glu Asp Arg Pro Leu Ser
                 85                  90                  95

GAC AAG GGC TCT GGA GAC AGC TCC CAG GTC ACT CAA GTC AGT CCC CAG     336
Asp Lys Gly Ser Gly Asp Ser Ser Gln Val Thr Gln Val Ser Pro Gln
            100                 105                 110

AGG ATT GCA CTC CGG CTC CGG CCA GAT GAT TCG AAG AAT TTC TCC ATC     384
Arg Ile Ala Leu Arg Leu Arg Pro Asp Asp Ser Lys Asn Phe Ser Ile
            115                 120                 125

CAA GTG CGG CAG GTG GAG GAT TAC CCT GTG GAC ATC TAC TAC TTG ATG     432
Gln Val Arg Gln Val Glu Asp Tyr Pro Val Asp Ile Tyr Tyr Leu Met
            130                 135                 140

GAC CTG TCT TAC TCC ATG AAG GAT GAT CTG TGG AGC ATC CAG AAC CTG     480
Asp Leu Ser Tyr Ser Met Lys Asp Asp Leu Trp Ser Ile Gln Asn Leu
145                 150                 155                 160

GGT ACC AAG CTG GCC ACC CAG ATG CGA AAG CTC ACC AGT AAC CTG CGG     528
Gly Thr Lys Leu Ala Thr Gln Met Arg Lys Leu Thr Ser Asn Leu Arg
                165                 170                 175

ATT GGC TTC GGG GCA TTT GTG GAC AAG CCT GTG TCA CCA TAC ATG TAT     576
Ile Gly Phe Gly Ala Phe Val Asp Lys Pro Val Ser Pro Tyr Met Tyr
            180                 185                 190

ATC TCC CCA CCA GAG GCC CTC GAA AAC CCC TGC TAT GAT ATG AAG ACC     624
Ile Ser Pro Pro Glu Ala Leu Glu Asn Pro Cys Tyr Asp Met Lys Thr
```

```
                195                 200                 205
ACC TGC TTG CCC ATG TTT GGC TAC AAA CAC GTG CTG ACG CTA ACT GAC         672
Thr Cys Leu Pro Met Phe Gly Tyr Lys His Val Leu Thr Leu Thr Asp
    210                 215                 220

CAG GTG ACC CGC TTC AAT GAG GAA GTG AAG AAG CAG AGT GTG TCA CGG         720
Gln Val Thr Arg Phe Asn Glu Glu Val Lys Lys Gln Ser Val Ser Arg
225                 230                 235                 240

AAC CGA GAT GCC CCA GAG GGT GGC TTT GAT GCC ATC ATG CAG GCT ACA         768
Asn Arg Asp Ala Pro Glu Gly Gly Phe Asp Ala Ile Met Gln Ala Thr
                245                 250                 255

GTC TGT GAT GAA AAG ATT GGC TGG AGG AAT                                 798
Val Cys Asp Glu Lys Ile Gly Trp Arg Asn
            260                 265

(2) INFORMATION FOR SEQ ID NO:3:

(i) SEQUENCE CHARACTERISTICS:
        (A) LENGTH: 266 amino acids
        (B) TYPE: amino acid
        (D) TOPOLOGY: linear (ii) MOLECULE TYPE: protein (xi) SEQUENCE DESCRIPTION: SEQ ID NO:3:

Met Arg Ala Arg Pro Arg Pro Arg Pro Leu Trp Val Thr Val Leu Ala
 1               5                  10                  15

Leu Gly Ala Leu Ala Gly Val Gly Val Gly Gly Pro Asn Ile Cys Thr
             20                  25                  30

Thr Arg Gly Val Ser Ser Cys Gln Gln Cys Leu Ala Val Ser Pro Met
         35                  40                  45

Cys Ala Trp Cys Ser Asp Glu Ala Leu Pro Leu Gly Ser Pro Arg Cys
     50                  55                  60

Asp Leu Lys Glu Asn Leu Leu Lys Asp Asn Cys Ala Pro Glu Ser Ile
 65                  70                  75                  80

Glu Phe Pro Val Ser Glu Ala Arg Val Leu Glu Asp Arg Pro Leu Ser
                 85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
        195                 200                 205

Thr Cys Leu Pro Met Phe Gly Tyr Lys His Val Leu Thr Leu Thr Asp
    210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                245                 250                 255

Val Cys Asp Glu Lys Ile Gly Trp Arg Asn
            260                 265
```

(2) INFORMATION FOR SEQ ID NO:4:

(i) SEQUENCE CHARACTERISTICS:
        (A) LENGTH: 798 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..798

(xi) SEQUENCE DESCRIPTION: SEQ ID NO:4:

```
ATG CGA GCG CGG CCG CGG CCC CGG CCG CTC TGG GTG ACT GTG CTG GCG      48
Met Arg Ala Arg Pro Arg Pro Arg Pro Leu Trp Val Thr Val Leu Ala
 1               5                  10                  15

CTG GGG GCG CTG GCG GGC GTT GGC GTA GGA GGG CCC AAC ATC TGT ACC      96
Leu Gly Ala Leu Ala Gly Val Gly Val Gly Gly Pro Asn Ile Cys Thr
             20                  25                  30

ACG CGA GGT GTG AGC TCC TGC CAG CAG TGC CTG GCT GTG AGC CCC ATG     144
Thr Arg Gly Val Ser Ser Cys Gln Gln Cys Leu Ala Val Ser Pro Met
         35                  40                  45

TGT GCC TGG TGC TCT GAT GAG GCC CTG CCT CCG GGC TCA CCT CGC TGT     192
Cys Ala Trp Cys Ser Asp Glu Ala Leu Pro Pro Gly Ser Pro Arg Cys
 50                  55                  60

GAC CTG AAG GAG AAT CTG CTG AAG GAT AAC TGT GCC CCA GAA TCC ATC     240
Asp Leu Lys Glu Asn Leu Leu Lys Asp Asn Cys Ala Pro Glu Ser Ile
 65                  70                  75                  80

GAG TTC CCA GTG AGT GAG GCC CGA GTA CTA GAG GAC AGG CCC CTC AGC     288
Glu Phe Pro Val Ser Glu Ala Arg Val Leu Glu Asp Arg Pro Leu Ser
             85                  90                  95

GAC AAG GGC TCT GGA GAC AGC TCC CAG GTC ACT CAA GTC AGT CCC CAG     336
Asp Lys Gly Ser Gly Asp Ser Ser Gln Val Thr Gln Val Ser Pro Gln
        100                 105                 110

AGG ATT GCA CTC CGG CTC CGG CCA GAT GAT TCG AAG AAT TTC TCC ATC     384
Arg Ile Ala Leu Arg Leu Arg Pro Asp Asp Ser Lys Asn Phe Ser Ile
        115                 120                 125

CAA GTG CGG CAG GTG GAG GAT TAC CCT GTG GAC ATC TAC TAC TTG ATG     432
Gln Val Arg Gln Val Glu Asp Tyr Pro Val Asp Ile Tyr Tyr Leu Met
130                 135                 140

GAC CTG TCT TAC TCC ATG AAG GAT GAT CTG TGG AGC ATC CAG AAC CTG     480
Asp Leu Ser Tyr Ser Met Lys Asp Asp Leu Trp Ser Ile Gln Asn Leu
145                 150                 155                 160

GGT ACC AAG CTG GCC ACC CAG ATG CGA AAG CTC ACC AGT AAC CTG CGG     528
Gly Thr Lys Leu Ala Thr Gln Met Arg Lys Leu Thr Ser Asn Leu Arg
                165                 170                 175

ATT GGC TTC GGG GCA TTT GTG GAC AAG CCT GTG TCA CCA TAC ATG TAT     576
Ile Gly Phe Gly Ala Phe Val Asp Lys Pro Val Ser Pro Tyr Met Tyr
            180                 185                 190

ATC TCC CCA CCA GAG GCC CTC GAA AAC CCC TGC TAT GAT ATG AAG ACC     624
Ile Ser Pro Pro Glu Ala Leu Glu Asn Pro Cys Tyr Asp Met Lys Thr
        195                 200                 205

ACC TGC TTG CCC ATG TTT GGC TAC AAA CAC GTG CTG ACG CTA ACT GAC     672
Thr Cys Leu Pro Met Phe Gly Tyr Lys His Val Leu Thr Leu Thr Asp
        210                 215                 220

CAG GTG ACC CGC TTC AAT GAG GAA GTG AAG AAG CAG AGT GTG TCA CGG     720
Gln Val Thr Arg Phe Asn Glu Glu Val Lys Lys Gln Ser Val Ser Arg
225                 230                 235                 240

AAC CGA GAT GCC CCA GAG GGT GGC TTT GAT GCC ATC ATG CAG GCT ACA     768
Asn Arg Asp Ala Pro Glu Gly Gly Phe Asp Ala Ile Met Gln Ala Thr
```

```
                    245                 250                 255
GTC TGT GAT GAA AAG ATT GGC TGG AGG AAT                              798
Val Cys Asp Glu Lys Ile Gly Trp Arg Asn
                260                 265
```

(2) INFORMATION FOR SEQ ID NO:5:

(i) SEQUENCE CHARACTERISTICS:
        (A) LENGTH: 266 amino acids
        (B) TYPE: amino acid
        (D) TOPOLOGY: linear (ii) MOLECULE TYPE: protein (xi) SEQUENCE DESCRIPTION: SEQ ID NO:5:

```
Met Arg Ala Arg Pro Arg Pro Arg Pro Leu Trp Val Thr Val Leu Ala
 1               5                  10                  15

Leu Gly Ala Leu Ala Gly Val Gly Val Gly Gly Pro Asn Ile Cys Thr
                20                  25                  30

Thr Arg Gly Val Ser Ser Cys Gln Gln Cys Leu Ala Val Ser Pro Met
            35                  40                  45

Cys Ala Trp Cys Ser Asp Glu Ala Leu Pro Pro Gly Ser Pro Arg Cys
    50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
        195                 200                 205

Thr Cys Leu Pro Met Phe Gly Tyr Lys His Val Leu Thr Leu Thr Asp
    210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                245                 250                 255

Val Cys Asp Glu Lys Ile Gly Trp Arg Asn
                260                 265
```

(2) INFORMATION FOR SEQ ID NO:6:

(i) SEQUENCE CHARACTERISTICS:
        (A) LENGTH: 195 base pairs
        (B) TYPE: nucleic acid
        (C) STRANDEDNESS: double
        (D) TOPOLOGY: linear (ii) MOLECULE TYPE: DNA (genomic)

(ix) FEATURE:
(A) NAME/KEY: CDS
(B) LOCATION: 1..195

(xi) SEQUENCE DESCRIPTION: SEQ ID NO:6:

```
GGG CCC AAC ATC TGT ACC ACG CGA GGT GTG AGC TCC TGC CAG CAG TGC    48
Gly Pro Asn Ile Cys Thr Thr Arg Gly Val Ser Ser Cys Gln Gln Cys
 1               5                  10                  15

CTG GCT GTG AGC CCC ATG TGT GCC TGG TGC TCT GAT GAG GCC CTG CCT    96
Leu Ala Val Ser Pro Met Cys Ala Trp Cys Ser Asp Glu Ala Leu Pro
                20                  25                  30

CTG GGC TCA CCT CGC TGT GAC CTG AAG GAG AAT CTG CTG AAG GAT AAC   144
Leu Gly Ser Pro Arg Cys Asp Leu Lys Glu Asn Leu Leu Lys Asp Asn
            35                  40                  45

TGT GCC CCA GAA TCC ATC GAG TTC CCA GTG AGT GAG GCC CGA GTA CTA   192
Cys Ala Pro Glu Ser Ile Glu Phe Pro Val Ser Glu Ala Arg Val Leu
        50                  55                  60

GAG                                                               195
Glu
65
```

(2) INFORMATION FOR SEQ ID NO:7:

(i) SEQUENCE CHARACTERISTICS:
(A) LENGTH: 65 amino acids
(B) TYPE: amino acid
(D) TOPOLOGY: linear (ii) MOLECULE TYPE: protein (xi) SEQUENCE DESCRIPTION: SEQ ID NO:7:

```
Gly Pro Asn Ile Cys Thr Thr Arg Gly Val Ser Ser Cys Gln Gln Cys
 1               5                  10                  15

Leu Ala Val Ser Pro Met Cys Ala Trp Cys Ser Asp Glu Ala Leu Pro
                20                  25                  30

Leu Gly Ser Pro Arg Cys Asp Leu Lys Glu Asn Leu Leu Lys Asp Asn
            35                  40                  45

Cys Ala Pro Glu Ser Ile Glu Phe Pro Val Ser Glu Ala Arg Val Leu
        50                  55                  60

Glu
65
```

(2) INFORMATION FOR SEQ ID NO:8:

(i) SEQUENCE CHARACTERISTICS:
(A) LENGTH: 195 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..195

(xi) SEQUENCE DESCRIPTION: SEQ ID NO:8:

```
GGG CCC AAC ATC TGT ACC ACG CGA GGT GTG AGC TCC TGC CAG CAG TGC    48
Gly Pro Asn Ile Cys Thr Thr Arg Gly Val Ser Ser Cys Gln Gln Cys
 1               5                  10                  15

CTG GCT GTG AGC CCC ATG TGT GCC TGG TGC TCT GAT GAG GCC CTG CCT    96
Leu Ala Val Ser Pro Met Cys Ala Trp Cys Ser Asp Glu Ala Leu Pro
                20                  25                  30

CCG GGC TCA CCT CGC TGT GAC CTG AAG GAG AAT CTG CTG AAG GAT AAC   144
Pro Gly Ser Pro Arg Cys Asp Leu Lys Glu Asn Leu Leu Lys Asp Asn
```

```
                 35                  40                  45
TGT GCC CCA GAA TCC ATC GAG TTC CCA GTG AGT GAG GCC CGA GTA CTA      192
Cys Ala Pro Glu Ser Ile Glu Phe Pro Val Ser Glu Ala Arg Val Leu
        50                  55                  60

GAG                                                                  195
Glu
65

(2) INFORMATION FOR SEQ ID NO:9:

(i) SEQUENCE CHARACTERISTICS:
        (A) LENGTH: 65 amino acids
        (B) TYPE: amino acid
        (D) TOPOLOGY: linear (ii) MOLECULE TYPE: protein (xi) SEQUENCE DESCRIPTION: SEQ ID NO:9:

Gly Pro Asn Ile Cys Thr Thr Arg Gly Val Ser Ser Cys Gln Gln Cys
 1               5                  10                  15

Leu Ala Val Ser Pro Met Cys Ala Trp Cys Ser Asp Glu Ala Leu Pro
                20                  25                  30

Pro Gly Ser Pro Arg Cys Asp Leu Lys Glu Asn Leu Leu Lys Asp Asn
            35                  40                  45

Cys Ala Pro Glu Ser Ile Glu Phe Pro Val Ser Glu Ala Arg Val Leu
        50                  55                  60

Glu
 65

(2) INFORMATION FOR SEQ ID NO:10:

(i) SEQUENCE CHARACTERISTICS:
        (A) LENGTH: 273 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..273

(xi) SEQUENCE DESCRIPTION: SEQ ID NO:10:

ATG CGA GCG CGG CCG CGG CCC CGG CCG CTC TGG GTG ACT GTG CTG GCG       48
Met Arg Ala Arg Pro Arg Pro Arg Pro Leu Trp Val Thr Val Leu Ala
 1               5                  10                  15

CTG GGG GCG CTG GCG GGC GTT GGC GTA GGA GGG CCC AAC ATC TGT ACC       96
Leu Gly Ala Leu Ala Gly Val Gly Val Gly Gly Pro Asn Ile Cys Thr
                20                  25                  30

ACG CGA GGT GTG AGC TCC TGC CAG CAG TGC CTG GCT GTG AGC CCC ATG      144
Thr Arg Gly Val Ser Ser Cys Gln Gln Cys Leu Ala Val Ser Pro Met
            35                  40                  45

TGT GCC TGG TGC TCT GAT GAG GCC CTG CCT CTG GGC TCA CCT CGC TGT      192
Cys Ala Trp Cys Ser Asp Glu Ala Leu Pro Leu Gly Ser Pro Arg Cys
        50                  55                  60

GAC CTG AAG GAG AAT CTG CTG AAG GAT AAC TGT GCC CCA GAA TCC ATC      240
Asp Leu Lys Glu Asn Leu Leu Lys Asp Asn Cys Ala Pro Glu Ser Ile
65                  70                  75                  80

GAG TTC CCA GTG AGT GAG GCC CGA GTA CTA GAG                          273
Glu Phe Pro Val Ser Glu Ala Arg Val Leu Glu
                85                  90

(2) INFORMATION FOR SEQ ID NO:11:
```

(i) SEQUENCE CHARACTERISTICS:
            (A) LENGTH: 91 amino acids
            (B) TYPE: amino acid
            (D) TOPOLOGY: linear (ii) MOLECULE TYPE: protein (xi) SEQUENCE DESCRIPTION: SEQ ID NO:11:

Met Arg Ala Arg Pro Arg Pro Arg Pro Leu Trp Val Thr Val Leu Ala
 1               5                  10                  15

Leu Gly Ala Leu Ala Gly Val Gly Val Gly Gly Pro Asn Ile Cys Thr
                20                  25                  30

Thr Arg Gly Val Ser Ser Cys Gln Gln Cys Leu Ala Val Ser Pro Met
            35                  40                  45

Cys Ala Trp Cys Ser Asp Glu Ala Leu Pro Leu Gly Ser Pro Arg Cys
 50                  55                  60

Asp Leu Lys Glu Asn Leu Leu Lys Asp Asn Cys Ala Pro Glu Ser Ile
 65                  70                  75                  80

Glu Phe Pro Val Ser Glu Ala Arg Val Leu Glu
                85                  90

(2) INFORMATION FOR SEQ ID NO:12:

(i) SEQUENCE CHARACTERISTICS:
            (A) LENGTH: 417 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 1..417

(xi) SEQUENCE DESCRIPTION: SEQ ID NO:12:

ATG CGA GCG CGG CCG CGG CCC CGG CCG CTC TGG GTG ACT GTG CTG GCG        48
Met Arg Ala Arg Pro Arg Pro Arg Pro Leu Trp Val Thr Val Leu Ala
 1               5                  10                  15

CTG GGG GCG CTG GCG GGC GTT GGC GTA GGA GGG CCC AAC ATC TGT ACC        96
Leu Gly Ala Leu Ala Gly Val Gly Val Gly Gly Pro Asn Ile Cys Thr
                20                  25                  30

ACG CGA GGT GTG AGC TCC TGC CAG CAG TGC CTG GCT GTG AGC CCC ATG       144
Thr Arg Gly Val Ser Ser Cys Gln Gln Cys Leu Ala Val Ser Pro Met
            35                  40                  45

TGT GCC TGG TGC TCT GAT GAG GCC CTG CCT CTG GGC TCA CCT CGC TGT       192
Cys Ala Trp Cys Ser Asp Glu Ala Leu Pro Leu Gly Ser Pro Arg Cys
 50                  55                  60

GAC CTG AAG GAG AAT CTG CTG AAG GAT AAC TGT GCC CCA GAA TCC ATC       240
Asp Leu Lys Glu Asn Leu Leu Lys Asp Asn Cys Ala Pro Glu Ser Ile
 65                  70                  75                  80

GAG TTC CCA GTG AGT GAG GCC CGA GTA CTA GAG GAC AGG CCC CTC AGC       288
Glu Phe Pro Val Ser Glu Ala Arg Val Leu Glu Asp Arg Pro Leu Ser
                85                  90                  95

GAC AAG GGC TCT GGA GAC AGC TCC CAG GTC ACT CAA GTC AGT CCC CAG       336
Asp Lys Gly Ser Gly Asp Ser Ser Gln Val Thr Gln Val Ser Pro Gln
            100                 105                 110

AGG ATT GCA CTC CGG CTC CGG CCA GAT GAT TCG AAG AAT TTC TCC ATC       384
Arg Ile Ala Leu Arg Leu Arg Pro Asp Asp Ser Lys Asn Phe Ser Ile
        115                 120                 125

CAA GTG CGG CAG GTG GAG GAT TAC CCT GTG GAC                           417
Gln Val Arg Gln Val Glu Asp Tyr Pro Val Asp
        130                 135

(2) INFORMATION FOR SEQ ID NO:13:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO:13:

```
Met Arg Ala Arg Pro Arg Pro Arg Pro Leu Trp Val Thr Val Leu Ala
 1               5                  10                  15

Leu Gly Ala Leu Ala Gly Val Gly Val Gly Gly Pro Asn Ile Cys Thr
             20                  25                  30

Thr Arg Gly Val Ser Ser Cys Gln Gln Cys Leu Ala Val Ser Pro Met
         35                  40                  45

Cys Ala Trp Cys Ser Asp Glu Ala Leu Pro Leu Gly Ser Pro Arg Cys
 50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                 85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp
    130                 135
```

(2) INFORMATION FOR SEQ ID NO:14:

(i) SEQUENCE CHARACTERISTICS:
        (A) LENGTH: 447 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..447

(xi) SEQUENCE DESCRIPTION: SEQ ID NO:14:

```
ATG CGA GCG CGG CCG CGG CCC CGG CCG CTC TGG GTG ACT GTG CTG GCG        48
Met Arg Ala Arg Pro Arg Pro Arg Pro Leu Trp Val Thr Val Leu Ala
 1               5                  10                  15

CTG GGG GCG CTG GCG GGC GTT GGC GTA GGA GGG CCC AAC ATC TGT ACC        96
Leu Gly Ala Leu Ala Gly Val Gly Val Gly Gly Pro Asn Ile Cys Thr
             20                  25                  30

ACG CGA GGT GTG AGC TCC TGC CAG CAG TGC CTG GCT GTG AGC CCC ATG       144
Thr Arg Gly Val Ser Ser Cys Gln Gln Cys Leu Ala Val Ser Pro Met
         35                  40                  45

TGT GCC TGG TGC TCT GAT GAG GCC CTG CCT CTG GGC TCA CCT CGC TGT       192
Cys Ala Trp Cys Ser Asp Glu Ala Leu Pro Leu Gly Ser Pro Arg Cys
 50                  55                  60

GAC CTG AAG GAG AAT CTG CTG AAG GAT AAC TGT GCC CCA GAA TCC ATC       240
Asp Leu Lys Glu Asn Leu Leu Lys Asp Asn Cys Ala Pro Glu Ser Ile
65                  70                  75                  80

GAG TTC CCA GTG AGT GAG GCC CGA GTA CTA GAG GAC AGG CCC CTC AGC       288
Glu Phe Pro Val Ser Glu Ala Arg Val Leu Glu Asp Arg Pro Leu Ser
                 85                  90                  95
```

```
GAC AAG GGC TCT GGA GAC AGC TCC CAG GTC ACT CAA GTC AGT CCC CAG       336
Asp Lys Gly Ser Gly Asp Ser Ser Gln Val Thr Gln Val Ser Pro Gln
            100                 105                 110

AGG ATT GCA CTC CGG CTC CGG CCA GAT GAT TCG AAG AAT TTC TCC ATC       384
Arg Ile Ala Leu Arg Leu Arg Pro Asp Asp Ser Lys Asn Phe Ser Ile
            115                 120                 125

CAA GTG CGG CAG GTG GAG GAT TAC CCT GTG GAC ATC TAC TAC TTG ATG       432
Gln Val Arg Gln Val Glu Asp Tyr Pro Val Asp Ile Tyr Tyr Leu Met
130                 135                 140

GAC CTG TCT TAC TCC                                                    447
Asp Leu Ser Tyr Ser
145
```

(2) INFORMATION FOR SEQ ID NO:15:

(i) SEQUENCE CHARACTERISTICS:
        (A) LENGTH: 149 amino acids
        (B) TYPE: amino acid
        (D) TOPOLOGY: linear (ii) MOLECULE TYPE: protein (xi) SEQUENCE DESCRIPTION: SEQ ID NO:15:

```
Met Arg Ala Arg Pro Arg Pro Arg Pro Leu Trp Val Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
            35                  40                  45

Cys Ala Trp Cys Ser Asp Glu Ala Leu Pro Leu Gly Ser Pro Arg Cys
    50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
            115                 120                 125

Gln Val Arg Gln Val Glu Asp Tyr Pro Val Asp Ile Tyr Tyr Leu Met
130                 135                 140

Asp Leu Ser Tyr Ser
145
```

(2) INFORMATION FOR SEQ ID NO:16:

(i) SEQUENCE CHARACTERISTICS:
        (A) LENGTH: 450 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..450

(xi) SEQUENCE DESCRIPTION: SEQ ID NO:16:

```
ATG CGA GCG CGG CCG CGG CCC CGG CCG CTC TGG GTG ACT GTG CTG GCG        48
Met Arg Ala Arg Pro Arg Pro Arg Pro Leu Trp Val Thr Val Leu Ala
1               5                   10                  15
```

| | | | | | | | | | | | | | | | | |
|---|---|---|---|---|---|---|---|---|---|---|---|---|---|---|---|---|
|CTG|GGG|GCG|CTG|GCG|GGC|GTT|GGC|GTA|GGA|GGG|CCC|AAC|ATC|TGT|ACC|96|
|Leu|Gly|Ala|Leu|Ala|Gly|Val|Gly|Val|Gly|Gly|Pro|Asn|Ile|Cys|Thr| |
| | |20| | | |25| | | | |30| | | | | |

| | | | | | | | | | | | | | | | | |
|---|---|---|---|---|---|---|---|---|---|---|---|---|---|---|---|---|
|ACG|CGA|GGT|GTG|AGC|TCC|TGC|CAG|CAG|TGC|CTG|GCT|GTG|AGC|CCC|ATG|144|
|Thr|Arg|Gly|Val|Ser|Ser|Cys|Gln|Gln|Cys|Leu|Ala|Val|Ser|Pro|Met| |
| | |35| | | |40| | | |45| | | | | | |

| | | | | | | | | | | | | | | | | |
|---|---|---|---|---|---|---|---|---|---|---|---|---|---|---|---|---|
|TGT|GCC|TGG|TGC|TCT|GAT|GAG|GCC|CTG|CCT|CTG|GGC|TCA|CCT|CGC|TGT|192|
|Cys|Ala|Trp|Cys|Ser|Asp|Glu|Ala|Leu|Pro|Leu|Gly|Ser|Pro|Arg|Cys| |
| |50| | | |55| | | |60| | | | | | | |

| | | | | | | | | | | | | | | | | |
|---|---|---|---|---|---|---|---|---|---|---|---|---|---|---|---|---|
|GAC|CTG|AAG|GAG|AAT|CTG|CTG|AAG|GAT|AAC|TGT|GCC|CCA|GAA|TCC|ATC|240|
|Asp|Leu|Lys|Glu|Asn|Leu|Leu|Lys|Asp|Asn|Cys|Ala|Pro|Glu|Ser|Ile| |
|65| | | |70| | | |75| | | | |80| | | |

| | | | | | | | | | | | | | | | | |
|---|---|---|---|---|---|---|---|---|---|---|---|---|---|---|---|---|
|GAG|TTC|CCA|GTG|AGT|GAG|GCC|CGA|GTA|CTA|GAG|GAC|AGG|CCC|CTC|AGC|288|
|Glu|Phe|Pro|Val|Ser|Glu|Ala|Arg|Val|Leu|Glu|Asp|Arg|Pro|Leu|Ser| |
| | | | |85| | | |90| | | | |95| | | |

| | | | | | | | | | | | | | | | | |
|---|---|---|---|---|---|---|---|---|---|---|---|---|---|---|---|---|
|GAC|AAG|GGC|TCT|GGA|GAC|AGC|TCC|CAG|GTC|ACT|CAA|GTC|AGT|CCC|CAG|336|
|Asp|Lys|Gly|Ser|Gly|Asp|Ser|Ser|Gln|Val|Thr|Gln|Val|Ser|Pro|Gln| |
| | | |100| | | |105| | | |110| | | | | |

| | | | | | | | | | | | | | | | | |
|---|---|---|---|---|---|---|---|---|---|---|---|---|---|---|---|---|
|AGG|ATT|GCA|CTC|CGG|CTC|CGG|CCA|GAT|GAT|TCG|AAG|AAT|TTC|TCC|ATC|384|
|Arg|Ile|Ala|Leu|Arg|Leu|Arg|Pro|Asp|Asp|Ser|Lys|Asn|Phe|Ser|Ile| |
| | |115| | | |120| | | |125| | | | | | |

| | | | | | | | | | | | | | | | | |
|---|---|---|---|---|---|---|---|---|---|---|---|---|---|---|---|---|
|CAA|GTG|CGG|CAG|GTG|GAG|GAT|TAC|CCT|GTG|GAC|ATC|TAC|TAC|TTG|ATG|432|
|Gln|Val|Arg|Gln|Val|Glu|Asp|Tyr|Pro|Val|Asp|Ile|Tyr|Tyr|Leu|Met| |
| |130| | | |135| | | |140| | | | | | | |

| | | | | | |
|---|---|---|---|---|---|---|
|GAC|CTG|TCT|TAC|TCC|ATG|450|
|Asp|Leu|Ser|Tyr|Ser|Met| |
|145| | | |150| | |

(2) INFORMATION FOR SEQ ID NO:17:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:17:

Met Arg Ala Arg Pro Arg Pro Arg Leu Trp Val Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
            35                  40              45

Cys Ala Trp Cys Ser Asp Glu Ala Leu Pro Leu Gly Ser Pro Arg Cys
    50              55              60

Asp Leu Lys Glu Asn Leu Leu Lys Asp Asn Cys Ala Pro Glu Ser Ile
65              70              75                  80

Glu Phe Pro Val Ser Glu Ala Arg Val Leu Glu Asp Arg Pro Leu Ser
                85              90                  95

Asp Lys Gly Ser Gly Asp Ser Ser Gln Val Thr Gln Val Ser Pro Gln
            100             105             110

Arg Ile Ala Leu Arg Leu Arg Pro Asp Asp Ser Lys Asn Phe Ser Ile
        115             120             125

Gln Val Arg Gln Val Glu Asp Tyr Pro Val Asp Ile Tyr Tyr Leu Met
    130             135             140

Asp Leu Ser Tyr Ser Met
145             150

(2) INFORMATION FOR SEQ ID NO:18:

(i) SEQUENCE CHARACTERISTICS:
    (A) LENGTH: 492 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: CDS
    (B) LOCATION: 1..492

(xi) SEQUENCE DESCRIPTION: SEQ ID NO:18:

| ATG | CGA | GCG | CGG | CCG | CGG | CCC | CGG | CCG | CTC | TGG | GTG | ACT | GTG | CTG | GCG | 48 |
| Met | Arg | Ala | Arg | Pro | Arg | Pro | Arg | Pro | Leu | Trp | Val | Thr | Val | Leu | Ala | |
| 1 | | | | 5 | | | | | 10 | | | | | 15 | | |

| CTG | GGG | GCG | CTG | GCG | GGC | GTT | GGC | GTA | GGA | GGG | CCC | AAC | ATC | TGT | ACC | 96 |
| Leu | Gly | Ala | Leu | Ala | Gly | Val | Gly | Val | Gly | Gly | Pro | Asn | Ile | Cys | Thr | |
| | | | 20 | | | | | 25 | | | | | 30 | | | |

| ACG | CGA | GGT | GTG | AGC | TCC | TGC | CAG | CAG | TGC | CTG | GCT | GTG | AGC | CCC | ATG | 144 |
| Thr | Arg | Gly | Val | Ser | Ser | Cys | Gln | Gln | Cys | Leu | Ala | Val | Ser | Pro | Met | |
| | | 35 | | | | | 40 | | | | | 45 | | | | |

| TGT | GCC | TGG | TGC | TCT | GAT | GAG | GCC | CTG | CCT | CTG | GGC | TCA | CCT | CGC | TGT | 192 |
| Cys | Ala | Trp | Cys | Ser | Asp | Glu | Ala | Leu | Pro | Leu | Gly | Ser | Pro | Arg | Cys | |
| 50 | | | | | 55 | | | | | 60 | | | | | | |

| GAC | CTG | AAG | GAG | AAT | CTG | CTG | AAG | GAT | AAC | TGT | GCC | CCA | GAA | TCC | ATC | 240 |
| Asp | Leu | Lys | Glu | Asn | Leu | Leu | Lys | Asp | Asn | Cys | Ala | Pro | Glu | Ser | Ile | |
| 65 | | | | 70 | | | | | 75 | | | | | 80 | | |

| GAG | TTC | CCA | GTG | AGT | GAG | GCC | CGA | GTA | CTA | GAG | GAC | AGG | CCC | CTC | AGC | 288 |
| Glu | Phe | Pro | Val | Ser | Glu | Ala | Arg | Val | Leu | Glu | Asp | Arg | Pro | Leu | Ser | |
| | | | | 85 | | | | | 90 | | | | | 95 | | |

| GAC | AAG | GGC | TCT | GGA | GAC | AGC | TCC | CAG | GTC | ACT | CAA | GTC | AGT | CCC | CAG | 336 |
| Asp | Lys | Gly | Ser | Gly | Asp | Ser | Ser | Gln | Val | Thr | Gln | Val | Ser | Pro | Gln | |
| | | | 100 | | | | | 105 | | | | | 110 | | | |

| AGG | ATT | GCA | CTC | CGG | CTC | CGG | CCA | GAT | GAT | TCG | AAG | AAT | TTC | TCC | ATC | 384 |
| Arg | Ile | Ala | Leu | Arg | Leu | Arg | Pro | Asp | Asp | Ser | Lys | Asn | Phe | Ser | Ile | |
| | | 115 | | | | | 120 | | | | | 125 | | | | |

| CAA | GTG | CGG | CAG | GTG | GAG | GAT | TAC | CCT | GTG | GAC | ATC | TAC | TAC | TTG | ATG | 432 |
| Gln | Val | Arg | Gln | Val | Glu | Asp | Tyr | Pro | Val | Asp | Ile | Tyr | Tyr | Leu | Met | |
| 130 | | | | | 135 | | | | | 140 | | | | | | |

| GAC | CTG | TCT | TAC | TCC | ATG | AAG | GAT | GAT | CTG | TGG | AGC | ATC | CAG | AAC | CTG | 480 |
| Asp | Leu | Ser | Tyr | Ser | Met | Lys | Asp | Asp | Leu | Trp | Ser | Ile | Gln | Asn | Leu | |
| 145 | | | | 150 | | | | | 155 | | | | | 160 | | |

| GGT | ACC | AAG | CTG | | | | | | | | | | | | | 492 |
| Gly | Thr | Lys | Leu | | | | | | | | | | | | | |

(2) INFORMATION FOR SEQ ID NO:19:

(i) SEQUENCE CHARACTERISTICS:
        (A) LENGTH: 164 amino acids
        (B) TYPE: amino acid
        (D) TOPOLOGY: linear (ii) MOLECULE TYPE: protein (xi) SEQUENCE DESCRIPTION: SEQ ID NO:19:

| Met | Arg | Ala | Arg | Pro | Arg | Pro | Arg | Pro | Leu | Trp | Val | Thr | Val | Leu | Ala |
| 1 | | | | 5 | | | | | 10 | | | | | 15 | |

| Leu | Gly | Ala | Leu | Ala | Gly | Val | Gly | Val | Gly | Gly | Pro | Asn | Ile | Cys | Thr |
| | | | 20 | | | | | 25 | | | | | 30 | | |

| Thr | Arg | Gly | Val | Ser | Ser | Cys | Gln | Gln | Cys | Leu | Ala | Val | Ser | Pro | Met |
| | | 35 | | | | | 40 | | | | | 45 | | | |

| Cys | Ala | Trp | Cys | Ser | Asp | Glu | Ala | Leu | Pro | Leu | Gly | Ser | Pro | Arg | Cys |

```
            50                  55                  60
Asp Leu Lys Glu Asn Leu Leu Lys Asp Asn Cys Ala Pro Glu Ser Ile
 65                  70                  75                  80

Glu Phe Pro Val Ser Glu Ala Arg Val Leu Glu Asp Arg Pro Leu Ser
                 85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140

Asp Leu Ser Tyr Ser Met Lys Asp Asp Leu Trp Ser Ile Gln Asn Leu
145                 150                 155                 160

Gly Thr Lys Leu (2) INFORMATION FOR SEQ ID NO:20:

(i) SEQUENCE CHARACTERISTICS:
         (A) LENGTH: 273 base pairs
         (B) TYPE: nucleic acid
         (C) STRANDEDNESS: double
         (D) TOPOLOGY: linear (ii) MOLECULE TYPE: DNA (genomic)

(ix) FEATURE:
         (A) NAME/KEY: CDS
         (B) LOCATION: 1..273

(xi) SEQUENCE DESCRIPTION: SEQ ID NO:20:

ATG CGA GCG CGG CCG CGG CCC CGG CCG CTC TGG GTG ACT GTG CTG GCG     48
Met Arg Ala Arg Pro Arg Pro Arg Pro Leu Trp Val Thr Val Leu Ala
 1               5                  10                  15

CTG GGG GCG CTG GCG GGC GTT GGC GTA GGA GGG CCC AAC ATC TGT ACC     96
Leu Gly Ala Leu Ala Gly Val Gly Val Gly Gly Pro Asn Ile Cys Thr
                20                  25                  30

ACG CGA GGT GTG AGC TCC TGC CAG CAG TGC CTG GCT GTG AGC CCC ATG    144
Thr Arg Gly Val Ser Ser Cys Gln Gln Cys Leu Ala Val Ser Pro Met
         35                  40                  45

TGT GCC TGG TGC TCT GAT GAG GCC CTG CCT CCG GGC TCA CCT CGC TGT    192
Cys Ala Trp Cys Ser Asp Glu Ala Leu Pro Pro Gly Ser Pro Arg Cys
     50                  55                  60

GAC CTG AAG GAG AAT CTG CTG AAG GAT AAC TGT GCC CCA GAA TCC ATC    240
Asp Leu Lys Glu Asn Leu Leu Lys Asp Asn Cys Ala Pro Glu Ser Ile
 65                  70                  75                  80

GAG TTC CCA GTG AGT GAG GCC CGA GTA CTA GAG                        273
Glu Phe Pro Val Ser Glu Ala Arg Val Leu Glu
                 85                  90

(2) INFORMATION FOR SEQ ID NO:21:

(i) SEQUENCE CHARACTERISTICS:
         (A) LENGTH: 91 amino acids
         (B) TYPE: amino acid
         (D) TOPOLOGY: linear (ii) MOLECULE TYPE: protein (xi) SEQUENCE DESCRIPTION: SEQ ID NO:21:

Met Arg Ala Arg Pro Arg Pro Arg Pro Leu Trp Val Thr Val Leu Ala
 1               5                  10                  15

Leu Gly Ala Leu Ala Gly Val Gly Val Gly Gly Pro Asn Ile Cys Thr
                20                  25                  30
```

```
Thr Arg Gly Val Ser Ser Cys Gln Gln Cys Leu Ala Val Ser Pro Met
        35                  40                  45

Cys Ala Trp Cys Ser Asp Glu Ala Leu Pro Pro Gly Ser Pro Arg Cys
 50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu
                85                  90
```

(2) INFORMATION FOR SEQ ID NO:22:

(i) SEQUENCE CHARACTERISTICS:
        (A) LENGTH: 417 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..417

(xi) SEQUENCE DESCRIPTION: SEQ ID NO:22:

```
ATG CGA GCG CGG CCG CGG CCC CGG CCG CTC TGG GTG ACT GTG CTG GCG     48
Met Arg Ala Arg Pro Arg Pro Arg Pro Leu Trp Val Thr Val Leu Ala
 1               5                  10                  15

CTG GGG GCG CTG GCG GGC GTT GGC GTA GGA GGG CCC AAC ATC TGT ACC     96
Leu Gly Ala Leu Ala Gly Val Gly Val Gly Gly Pro Asn Ile Cys Thr
                20                  25                  30

ACG CGA GGT GTG AGC TCC TGC CAG CAG TGC CTG GCT GTG AGC CCC ATG    144
Thr Arg Gly Val Ser Ser Cys Gln Gln Cys Leu Ala Val Ser Pro Met
            35                  40                  45

TGT GCC TGG TGC TCT GAT GAG GCC CTG CCT CCG GGC TCA CCT CGC TGT    192
Cys Ala Trp Cys Ser Asp Glu Ala Leu Pro Pro Gly Ser Pro Arg Cys
 50                  55                  60

GAC CTG AAG GAG AAT CTG CTG AAG GAT AAC TGT GCC CCA GAA TCC ATC    240
Asp Leu Lys Glu Asn Leu Leu Lys Asp Asn Cys Ala Pro Glu Ser Ile
65                  70                  75                  80

GAG TTC CCA GTG AGT GAG GCC CGA GTA CTA GAG GAC AGG CCC CTC AGC    288
Glu Phe Pro Val Ser Glu Ala Arg Val Leu Glu Asp Arg Pro Leu Ser
                85                  90                  95

GAC AAG GGC TCT GGA GAC AGC TCC CAG GTC ACT CAA GTC AGT CCC CAG    336
Asp Lys Gly Ser Gly Asp Ser Ser Gln Val Thr Gln Val Ser Pro Gln
              100                 105                 110

AGG ATT GCA CTC CGG CTC CGG CCA GAT GAT TCG AAG AAT TTC TCC ATC    384
Arg Ile Ala Leu Arg Leu Arg Pro Asp Asp Ser Lys Asn Phe Ser Ile
            115                 120                 125

CAA GTG CGG CAG GTG GAG GAT TAC CCT GTG GAC                        417
Gln Val Arg Gln Val Glu Asp Tyr Pro Val Asp
        130                 135
```

(2) INFORMATION FOR SEQ ID NO:23:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO:23:

```
Met Arg Ala Arg Pro Arg Pro Arg Pro Leu Trp Val Thr Val Leu Ala
 1               5                  10                  15
```

```
Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
        35                  40                  45

Cys Ala Trp Cys Ser Asp Glu Ala Leu Pro Pro Gly Ser Pro Arg Cys
50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp
130                 135
```

(2) INFORMATION FOR SEQ ID NO:24:

(i) SEQUENCE CHARACTERISTICS:
        (A) LENGTH: 447 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..447

(xi) SEQUENCE DESCRIPTION: SEQ ID NO:24:

```
ATG CGA GCG CGG CCG CGG CCC CGG CCG CTC TGG GTG ACT GTG CTG GCG    48
Met Arg Ala Arg Pro Arg Pro Arg Pro Leu Trp Val Thr Val Leu Ala
1               5                   10                  15

CTG GGG GCG CTG GCG GGC GTT GGC GTA GGA GGG CCC AAC ATC TGT ACC    96
Leu Gly Ala Leu Ala Gly Val Gly Val Gly Gly Pro Asn Ile Cys Thr
            20                  25                  30

ACG CGA GGT GTG AGC TCC TGC CAG CAG TGC CTG GCT GTG AGC CCC ATG   144
Thr Arg Gly Val Ser Ser Cys Gln Gln Cys Leu Ala Val Ser Pro Met
        35                  40                  45

TGT GCC TGG TGC TCT GAT GAG GCC CTG CCT CCG GGC TCA CCT CGC TGT   192
Cys Ala Trp Cys Ser Asp Glu Ala Leu Pro Pro Gly Ser Pro Arg Cys
50                  55                  60

GAC CTG AAG GAG AAT CTG CTG AAG GAT AAC TGT GCC CCA GAA TCC ATC   240
Asp Leu Lys Glu Asn Leu Leu Lys Asp Asn Cys Ala Pro Glu Ser Ile
65                  70                  75                  80

GAG TTC CCA GTG AGT GAG GCC CGA GTA CTA GAG GAC AGG CCC CTC AGC   288
Glu Phe Pro Val Ser Glu Ala Arg Val Leu Glu Asp Arg Pro Leu Ser
                85                  90                  95

GAC AAG GGC TCT GGA GAC AGC TCC CAG GTC ACT CAA GTC AGT CCC CAG   336
Asp Lys Gly Ser Gly Asp Ser Ser Gln Val Thr Gln Val Ser Pro Gln
            100                 105                 110

AGG ATT GCA CTC CGG CTC CGG CCA GAT GAT TCG AAG AAT TTC TCC ATC   384
Arg Ile Ala Leu Arg Leu Arg Pro Asp Asp Ser Lys Asn Phe Ser Ile
        115                 120                 125

CAA GTG CGG CAG GTG GAG GAT TAC CCT GTG GAC ATC TAC TAC TTG ATG   432
Gln Val Arg Gln Val Glu Asp Tyr Pro Val Asp Ile Tyr Tyr Leu Met
130                 135                 140

GAC CTG TCT TAC TCC                                                447
Asp Leu Ser Tyr Ser
```

5,939,524

67

68

-continued

145

(2) INFORMATION FOR SEQ ID NO:25:

(i) SEQUENCE CHARACTERISTICS:
(A) LENGTH: 149 amino acids
(B) TYPE: amino acid
(D) TOPOLOGY: linear (ii) MOLECULE TYPE: protein (xi) SEQUENCE DESCRIPTION: SEQ ID NO:25:

```
Met Arg Ala Arg Pro Arg Pro Arg Pro Leu Trp Val Thr Val Leu Ala
  1               5                  10                  15

Leu Gly Ala Leu Ala Gly Val Gly Val Gly Gly Pro Asn Ile Cys Thr
                 20                  25                  30

Thr Arg Gly Val Ser Ser Cys Gln Gln Cys Leu Ala Val Ser Pro Met
             35                  40                  45

Cys Ala Trp Cys Ser Asp Glu Ala Leu Pro Pro Gly Ser Pro Arg Cys
 50                  55                  60

Asp Leu Lys Glu Asn Leu Leu Lys Asp Asn Cys Ala Pro Glu Ser Ile
 65                  70                  75                  80

Glu Phe Pro Val Ser Glu Ala Arg Val Leu Glu Asp Arg Pro Leu Ser
                 85                  90                  95

Asp Lys Gly Ser Gly Asp Ser Ser Gln Val Thr Gln Val Ser Pro Gln
                100                 105                 110

Arg Ile Ala Leu Arg Leu Arg Pro Asp Asp Ser Lys Asn Phe Ser Ile
            115                 120                 125

Gln Val Arg Gln Val Glu Asp Tyr Pro Val Asp Ile Tyr Tyr Leu Met
        130                 135                 140

Asp Leu Ser Tyr Ser
145
```

(2) INFORMATION FOR SEQ ID NO:26:

(i) SEQUENCE CHARACTERISTICS:
(A) LENGTH: 450 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..450

(xi) SEQUENCE DESCRIPTION: SEQ ID NO:26:

```
ATG CGA GCG CGG CCG CGG CCC CGG CCG CTC TGG GTG ACT GTG CTG GCG        48
Met Arg Ala Arg Pro Arg Pro Arg Pro Leu Trp Val Thr Val Leu Ala
 1               5                  10                  15

CTG GGG GCG CTG GCG GGC GTT GGC GTA GGA GGG CCC AAC ATC TGT ACC        96
Leu Gly Ala Leu Ala Gly Val Gly Val Gly Gly Pro Asn Ile Cys Thr
                 20                  25                  30

ACG CGA GGT GTG AGC TCC TGC CAG CAG TGC CTG GCT GTG AGC CCC ATG       144
Thr Arg Gly Val Ser Ser Cys Gln Gln Cys Leu Ala Val Ser Pro Met
             35                  40                  45

TGT GCC TGG TGC TCT GAT GAG GCC CTG CCT CCG GGC TCA CCT CGC TGT       192
Cys Ala Trp Cys Ser Asp Glu Ala Leu Pro Pro Gly Ser Pro Arg Cys
 50                  55                  60

GAC CTG AAG GAG AAT CTG CTG AAG GAT AAC TGT GCC CCA GAA TCC ATC       240
Asp Leu Lys Glu Asn Leu Leu Lys Asp Asn Cys Ala Pro Glu Ser Ile
 65                  70                  75                  80
```

```
GAG TTC CCA GTG AGT GAG GCC CGA GTA CTA GAG GAC AGG CCC CTC AGC    288
Glu Phe Pro Val Ser Glu Ala Arg Val Leu Glu Asp Arg Pro Leu Ser
                85                  90                  95

GAC AAG GGC TCT GGA GAC AGC TCC CAG GTC ACT CAA GTC AGT CCC CAG    336
Asp Lys Gly Ser Gly Asp Ser Ser Gln Val Thr Gln Val Ser Pro Gln
            100                 105                 110

AGG ATT GCA CTC CGG CTC CGG CCA GAT GAT TCG AAG AAT TTC TCC ATC    384
Arg Ile Ala Leu Arg Leu Arg Pro Asp Asp Ser Lys Asn Phe Ser Ile
        115                 120                 125

CAA GTG CGG CAG GTG GAG GAT TAC CCT GTG GAC ATC TAC TAC TTG ATG    432
Gln Val Arg Gln Val Glu Asp Tyr Pro Val Asp Ile Tyr Tyr Leu Met
    130                 135                 140

GAC CTG TCT TAC TCC ATG                                            450
Asp Leu Ser Tyr Ser Met
145                 150
```

(2) INFORMATION FOR SEQ ID NO:27:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:27:

```
Met Arg Ala Arg Pro Arg Pro Arg Pro Leu Trp Val Thr Val Leu Ala
 1               5                  10                  15

Leu Gly Ala Leu Ala Gly Val Gly Val Gly Gly Pro Asn Ile Cys Thr
                20                  25                  30

Thr Arg Gly Val Ser Ser Cys Gln Gln Cys Leu Ala Val Ser Pro Met
        35                  40                  45

Cys Ala Trp Cys Ser Asp Glu Ala Leu Pro Pro Gly Ser Pro Arg Cys
    50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140

Asp Leu Ser Tyr Ser Met
145                 150
```

(2) INFORMATION FOR SEQ ID NO:28:

(i) SEQUENCE CHARACTERISTICS:
        (A) LENGTH: 492 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..492

(xi) SEQUENCE DESCRIPTION: SEQ ID NO:28:

```
ATG CGA GCG CGG CCG CGG CCC CGG CCG CTC TGG GTG ACT GTG CTG GCG        48
Met Arg Ala Arg Pro Arg Pro Arg Pro Leu Trp Val Thr Val Leu Ala
 1               5                  10                  15

CTG GGG GCG CTG GCG GGC GTT GGC GTA GGA GGG CCC AAC ATC TGT ACC        96
Leu Gly Ala Leu Ala Gly Val Gly Val Gly Gly Pro Asn Ile Cys Thr
             20                  25                  30

ACG CGA GGT GTG AGC TCC TGC CAG CAG TGC CTG GCT GTG AGC CCC ATG       144
Thr Arg Gly Val Ser Ser Cys Gln Gln Cys Leu Ala Val Ser Pro Met
         35                  40                  45

TGT GCC TGG TGC TCT GAT GAG GCC CTG CCT CCG GGC TCA CCT CGC TGT       192
Cys Ala Trp Cys Ser Asp Glu Ala Leu Pro Pro Gly Ser Pro Arg Cys
     50                  55                  60

GAC CTG AAG GAG AAT CTG CTG AAG GAT AAC TGT GCC CCA GAA TCC ATC       240
Asp Leu Lys Glu Asn Leu Leu Lys Asp Asn Cys Ala Pro Glu Ser Ile
 65                  70                  75                  80

GAG TTC CCA GTG AGT GAG GCC CGA GTA CTA GAG GAC AGG CCC CTC AGC       288
Glu Phe Pro Val Ser Glu Ala Arg Val Leu Glu Asp Arg Pro Leu Ser
                 85                  90                  95

GAC AAG GGC TCT GGA GAC AGC TCC CAG GTC ACT CAA GTC AGT CCC CAG       336
Asp Lys Gly Ser Gly Asp Ser Ser Gln Val Thr Gln Val Ser Pro Gln
            100                 105                 110

AGG ATT GCA CTC CGG CTC CGG CCA GAT GAT TCG AAG AAT TTC TCC ATC       384
Arg Ile Ala Leu Arg Leu Arg Pro Asp Asp Ser Lys Asn Phe Ser Ile
        115                 120                 125

CAA GTG CGG CAG GTG GAG GAT TAC CCT GTG GAC ATC TAC TAC TTG ATG       432
Gln Val Arg Gln Val Glu Asp Tyr Pro Val Asp Ile Tyr Tyr Leu Met
    130                 135                 140

GAC CTG TCT TAC TCC ATG AAG GAT GAT CTG TGG AGC ATC CAG AAC CTG       480
Asp Leu Ser Tyr Ser Met Lys Asp Asp Leu Trp Ser Ile Gln Asn Leu
145                 150                 155                 160

GGT ACC AAG CTG                                                       492
Gly Thr Lys Leu
```

(2) INFORMATION FOR SEQ ID NO:29:

(i) SEQUENCE CHARACTERISTICS:
        (A) LENGTH: 164 amino acids
        (B) TYPE: amino acid
        (D) TOPOLOGY: linear (ii) MOLECULE TYPE: protein (xi) SEQUENCE DESCRIPTION: SEQ ID NO:29:

```
Met Arg Ala Arg Pro Arg Pro Arg Pro Leu Trp Val Thr Val Leu Ala
 1               5                  10                  15

Leu Gly Ala Leu Ala Gly Val Gly Val Gly Gly Pro Asn Ile Cys Thr
             20                  25                  30

Thr Arg Gly Val Ser Ser Cys Gln Gln Cys Leu Ala Val Ser Pro Met
         35                  40                  45

Cys Ala Trp Cys Ser Asp Glu Ala Leu Pro Pro Gly Ser Pro Arg Cys
     50                  55                  60

Asp Leu Lys Glu Asn Leu Leu Lys Asp Asn Cys Ala Pro Glu Ser Ile
 65                  70                  75                  80

Glu Phe Pro Val Ser Glu Ala Arg Val Leu Glu Asp Arg Pro Leu Ser
                 85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
```

```
                    130                 135                 140
Asp Leu Ser Tyr Ser Met Lys Asp Asp Leu Trp Ser Ile Gln Asn Leu
145                 150                 155                 160

Gly Thr Lys Leu (2) INFORMATION FOR SEQ ID NO:30:

(i) SEQUENCE CHARACTERISTICS:
        (A) LENGTH: 8 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:30:

GGTCGACC                                                                        8

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GGTGAGCCCG GAGGCAGGGC CTCA                                                     24

(2) INFORMATION FOR SEQ ID NO:32:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

ATCGAGGGAA GGATTTCAGA ATTCGGATCC TCTAGAGTCG ACCTGCAGGC AAGCTTG                 57
```